US009776755B2

(12) United States Patent
Kondo et al.

(10) Patent No.: US 9,776,755 B2
(45) Date of Patent: Oct. 3, 2017

(54) DRUG SUPPLY DEVICE AND DRUG INSPECTION METHOD IN DRUG SUPPLY DEVICE

(71) Applicant: Panasonic Healthcare Co., Ltd., Ehime (JP)

(72) Inventors: Akira Kondo, Ehime (JP); Hideyuki Takahashi, Ehime (JP); Takashi Mori, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 545 days.

(21) Appl. No.: 14/329,716

(22) Filed: Jul. 11, 2014

(65) Prior Publication Data

US 2014/0318078 A1 Oct. 30, 2014

Related U.S. Application Data

(63) Continuation of application No. PCT/JP2012/008372, filed on Dec. 27, 2012.

(30) Foreign Application Priority Data

Jan. 11, 2012 (JP) ................................. 2012-002754

(51) Int. Cl.
*B65B 57/14* (2006.01)
*B65B 57/10* (2006.01)
(Continued)

(52) U.S. Cl.
CPC .............. *B65B 57/14* (2013.01); *B65B 5/103* (2013.01); *B65B 57/10* (2013.01); *G07F 9/026* (2013.01);
(Continued)

(58) Field of Classification Search
CPC ......... B65B 5/103; B65B 5/101; B65B 57/20; B65B 65/08; G07F 17/0092; G07F 11/44; G06T 7/60; A61J 7/02; G06K 9/3241
(Continued)

(56) References Cited

U.S. PATENT DOCUMENTS 5,097,652 A * 3/1992 Inamura .................. B65B 5/103
53/154
5,097,982 A * 3/1992 Kedem .................. A61J 7/0084
221/126
(Continued)

FOREIGN PATENT DOCUMENTS

| JP | 7-200770 A | 8/1995 |
| JP | 11-206855 A | 8/1999 |
| JP | 2011-104077 A | 6/2011 |

OTHER PUBLICATIONS

International Search Report issued in International Application No. PCT/JP2012/008372, dated Mar. 19, 2013, with English translation.

*Primary Examiner* — Thanh Truong
*Assistant Examiner* — Dariush Seif
(74) *Attorney, Agent, or Firm* — McDermott Will & Emery LLP

(57) ABSTRACT

A drug supply device includes a hopper that collects solid drugs discharged from tablet cases on the basis of predetermined prescription data, an inspection device that inspects the solid drugs introduced from the hopper, and a packaging device that fills and packages the inspected solid drugs into a packaging sheet. The inspection device includes inspection containers that each hold a single administration dosage of the solid drugs, a movement mechanism that moves the inspection containers, and an imaging device that captures an image of the solid drugs in the inspection containers. As a result of capturing the image of the solid drugs in the inspection container by the imaging device, when a number (Continued)

of the solid drugs is different from the prescription data, the solid drugs are disposed of.

10 Claims, 10 Drawing Sheets

(51) Int. Cl.
| | |
|---|---|
| *G07F 9/02* | (2006.01) |
| *G07F 11/62* | (2006.01) |
| *G07F 17/00* | (2006.01) |
| *B65B 5/10* | (2006.01) |
| G06F 19/00 | (2011.01) |
| A61J 7/00 | (2006.01) |
| B65B 61/02 | (2006.01) |
| B65B 61/06 | (2006.01) |
| B65B 9/06 | (2012.01) |
| G01N 21/95 | (2006.01) |

(52) U.S. Cl.
CPC .......... *G07F 11/62* (2013.01); *G07F 17/0092* (2013.01); *A61J 7/0084* (2013.01); *B65B 9/06* (2013.01); *B65B 61/025* (2013.01); *B65B 61/06* (2013.01); *G01N 21/9508* (2013.01); *G06F 19/3462* (2013.01)

(58) Field of Classification Search
USPC ... 53/500, 64, 493, 498, 501, 503, 450, 451, 53/455, 459, 550–555, 562, 568, 167; 382/192, 128, 110, 165, 190, 195
See application file for complete search history.

(56) References Cited

U.S. PATENT DOCUMENTS

| | | | | |
|---|---|---|---|---|
| 5,219,095 A * | 6/1993 | Shimizu | G07F 17/0092 | 221/264 |
| 5,481,855 A * | 1/1996 | Yuyama | B65B 1/06 | 53/168 |
| 5,638,657 A * | 6/1997 | Archer | B07C 5/342 | 53/244 |
| 5,667,096 A * | 9/1997 | Wu | G07F 17/0092 | 221/130 |
| 5,671,592 A * | 9/1997 | Yuyama | G07F 17/0092 | 53/168 |
| 5,709,063 A * | 1/1998 | Yuyama | B65B 1/06 | 53/154 |
| 5,752,368 A * | 5/1998 | Tobe | B65B 5/103 | 221/3 |
| 5,765,606 A * | 6/1998 | Takemasa | G07F 17/0092 | 141/104 |
| 5,803,309 A * | 9/1998 | Yuyama | G07F 17/0092 | 221/27 |
| 5,839,257 A * | 11/1998 | Soderstrom | B65B 61/26 | 53/131.5 |
| 5,852,911 A * | 12/1998 | Yuyama | B65B 35/04 | 221/10 |
| 5,963,453 A * | 10/1999 | East | G06F 19/3462 | 53/493 |
| 6,170,229 B1 * | 1/2001 | Kim | B65B 35/56 | 221/265 |
| 6,170,230 B1 * | 1/2001 | Chudy | B65B 5/103 | 53/168 |
| 6,170,699 B1 * | 1/2001 | Kim | G07F 11/58 | 221/253 |
| 6,308,494 B1 * | 10/2001 | Yuyama | B65B 5/103 | 53/131.3 |
| 6,324,253 B1 * | 11/2001 | Yuyama | G01N 23/04 | 209/589 |
| 6,330,351 B1 * | 12/2001 | Yasunaga | G01N 21/9508 | 235/375 |
| 6,394,308 B1 * | 5/2002 | Yuyama | B65G 47/1457 | 221/119 |
| 6,449,921 B1 * | 9/2002 | Kim | B65B 5/103 | 53/154 |
| 6,535,637 B1 * | 3/2003 | Wootton | B65B 57/00 | 221/102 |
| 6,581,356 B2 * | 6/2003 | Kim | B65B 5/103 | 221/119 |
| 6,690,998 B1 * | 2/2004 | Yuyama | B65B 5/103 | 193/14 |
| 6,705,487 B2 * | 3/2004 | Kim | B65B 35/56 | 141/247 |
| 6,772,907 B2 * | 8/2004 | Kim | B65B 5/103 | 221/131 |
| 6,799,684 B2 * | 10/2004 | Wooldridge | B07C 5/38 | 209/551 |
| 6,839,403 B1 * | 1/2005 | Kotowski | G01V 5/0083 | 378/57 |
| 6,898,919 B2 * | 5/2005 | Kim | G07F 17/0092 | 221/123 |
| 7,451,583 B2 * | 11/2008 | Kim | B65B 5/103 | 221/125 |
| 7,641,073 B2 * | 1/2010 | Kim | B65B 5/103 | 221/171 |
| 7,894,656 B2 * | 2/2011 | Kim | G07F 11/00 | 382/141 |
| 8,186,542 B2 * | 5/2012 | Kobayashi | G07F 9/02 | 221/124 |
| 8,234,838 B2 * | 8/2012 | Yasunaga | A61J 7/0084 | 221/123 |
| 8,579,153 B2 * | 11/2013 | Yuyama | B65B 5/103 | 221/130 |
| 8,615,971 B2 * | 12/2013 | Freudelsperger | B65B 5/103 | 53/154 |
| 8,769,915 B2 * | 7/2014 | Kobayashi | B65B 5/103 | 53/244 |
| 8,782,999 B2 * | 7/2014 | Kondo | B65B 5/103 | 53/244 |
| 8,950,625 B2 * | 2/2015 | Brug | B65H 3/00 | 221/231 |
| 9,238,518 B2 * | 1/2016 | Luciano, Jr. | B65D 75/42 | |
| 9,299,212 B2 * | 3/2016 | Amano | G07F 11/44 | |
| 9,333,541 B2 * | 5/2016 | Yasunaga | B08B 7/02 | |
| 9,334,096 B2 * | 5/2016 | Luciano, Jr. | B65D 75/36 | |
| 2001/0041968 A1 * | 11/2001 | Hamilton | A61J 7/02 | 702/128 |
| 2004/0011806 A1 * | 1/2004 | Luciano | B65B 37/08 | 221/266 |
| 2006/0058724 A1 * | 3/2006 | Handfield | A61J 7/0084 | 604/20 |
| 2008/0110131 A1 * | 5/2008 | Kim | G06F 19/3462 | 53/154 |
| 2010/0076595 A1 * | 3/2010 | Nguyen | A61J 7/0084 | 700/232 |
| 2010/0147734 A1 * | 6/2010 | Luciano, Jr. | G06F 19/328 | 206/534 |
| 2010/0287880 A1 * | 11/2010 | Yasunaga | A61J 7/0084 | 53/64 |
| 2011/0153066 A1 * | 6/2011 | Terzini | B65B 5/103 | 700/231 |
| 2012/0116579 A1 * | 5/2012 | Shows | G06F 19/3462 | 700/236 |
| 2012/0200596 A1 * | 8/2012 | Gotou | B07C 5/38 | 345/625 |
| 2012/0216485 A1 * | 8/2012 | Amano | G07F 11/44 | 53/64 |
| 2012/0296592 A1 * | 11/2012 | Luciano, Jr. | B65D 75/36 | 702/84 |
| 2013/0101377 A1 * | 4/2013 | Hawkes | B65G 47/28 | 414/589 |
| 2014/0002631 A1 * | 1/2014 | Amano | H04N 7/18 | 348/86 |

(56) References Cited

U.S. PATENT DOCUMENTS

2015/0154750 A1* 6/2015 Royaee ................ G06K 9/6267
                                                  382/128
2015/0190312 A1* 7/2015 Yuyama .............. G06F 19/3462
                                                  700/232
2016/0104282 A1* 4/2016 Takahashi ............... B65B 37/04
                                                  382/103

* cited by examiner

DRUG SUPPLY DEVICE AND DRUG INSPECTION METHOD IN DRUG SUPPLY DEVICE

RELATED APPLICATIONS

This application is the is a continuation of International Application No. PCT/JP2012/008372, filed on Dec. 27, 2012, which in turn claims the benefit of Japanese Application No. 2012-002754, filed on Jan. 11, 2012, the disclosures of which are incorporated by reference herein.

TECHNICAL FIELD

The present invention relates to a drug supply device, which is installed in a hospital, a pharmacy or the like and which is designed for filling and packaging solid drugs (hereinafter solid drugs refers to all solidified drug products including tablets, capsules, pills, and lozenges) specified by a prescription into a packaging sheet, and also relates to a drug inspection method provided in the drug supply device.

BACKGROUND ART

Conventionally, in a hospital or the like, a solid drug supply device is publicly known that supplies each patient with multiple types of tablets or capsule drugs (hereinafter these drugs are referred to as solid drugs) that are prescribed by a doctor for each of the patients, by separately packaging each of a single administration dosage of the drugs (a single administration dosage) into a divided package. However, it becomes important to check that the correct number of the solid drugs prescribed by the doctor is actually separately packaged into each of the divided packages. As an inspection device for inspecting the above-described number, there is a device that captures an image of the solid drugs in a state of being separately packaged into the divided package, and by doing so, checks that the correct number of the solid drugs prescribed by the doctor is separately packaged into each of the divided packages (refer to Patent Literature 1).

CITATION LIST

Patent Literature

Patent Literature 1: Japanese Patent Application Laid-Open No. Hei. 7-200770

SUMMARY OF INVENTION

Technical Problem

In a solid drug supply device disclosed in Patent Literature 1, since an image is captured of the drugs are in a state of being separately packaged in a divided package, in a case when the drugs are overlapping with one another, the number of the drugs may not be determined accurately. Further, when it is detected by the imaging that a predetermined number of the drugs is not packaged in a packaging sheet, not only the detected section of the packaging sheet but also a series of sections of the packaging sheet, which are planned to be used for separately packaging the drugs, are separated and discarded, and it is necessary to once more restart the solid drug supply device on the basis of desired prescription data. As a result, an excessive amount of the packaging sheet is disposed of, and furthermore, as the separating and disposal operation is handled manually by an operator, a rather burdensome operation is generated in terms of operating the solid drug supply device.

In the light of the foregoing, the present invention provides a solid drug supply device that captures an image of solid drugs before the solid drugs are separately packaged into a divided package. Based on the imaging, when it is determined that a number of the solid drugs is not as specified by prescription data, the solid drug supply device disposes of the solid drugs and then discharges a correct number of the solid drugs from tablet cases again. Then, by capturing an image and inspecting the number of the drugs again, the solid drug supply device ensures that the solid drugs based on the prescription data are always packaged at a stage at which the solid drugs are separately packaged into the divided package.

Therefore, the present invention achieves the above-described object by performing: an imaging step of capturing an image of drugs in a state in which the drugs discharged from the tablet cases are received, at a stage before the drugs that are discharged from the tablet cases based on the desired prescription data are filled and packaged into a divided packaging sheet (also described as separately packaged); a filling step at which a packaging device can fill and package the drugs into a packaging sheet when it is determined, on the basis of the imaging, that the number of the solid drugs is as specified by the desired prescription data; a disposal step of disposing of the drugs when it is determined, on the basis of the imaging, that the number of the solid drugs is not as specified by the desired prescription data; and a process in which, when the drugs are disposed of, the correct number of the solid drugs is once more discharged from the tablet cases and an image of the drugs discharged from the tablet cases is once more captured at the above-described imaging step.

Further, in order to promote downsizing of the solid drug supply device, the present invention has a structure in which each of the above-described steps can be performed on the basis of a planar rotation operation.

Further, in the present invention, when a prescription is printed by a printing mechanism on a surface of the packaging sheet on the basis of the desired prescription data, printing is normally performed before the drugs are filled into the packaging sheet, since it is not possible to perform the printing at a stage when the drugs are already filled into the packaging sheet, as the drugs obstruct the printing. In the present invention, the printing mechanism performs the printing only after it is determined that the number of the solid drugs is as specified by the prescription data in the above-described manner. Therefore, as described above, when it is determined that the number of the drugs is not as specified by the prescription data, the drugs are disposed of, and the printing mechanism performs the printing only after it is determined that the number of solid drugs once more discharged from the tablet cases is as specified by the prescription data. Based on the above-described structure, the present invention provides a solid drug supply device capable of eliminating wasteful disposal of a packaging sheet and a resulting disposal operation.

Solution to Problem

A drug supply device of a first aspect of the present invention is characterized by providing a solid drug supply device that includes: a plurality of tablet cases in which solid drugs are stored while being categorized by type; a hopper that collects solid drugs discharged from the tablet cases on the basis of predetermined prescription data; an inspection device that inspects the solid drugs discharged by the hopper; and a packaging device that fills and packages the solid drugs inspected by the inspection device into a packaging sheet, wherein the inspection device includes: an inspection container that holds the solid drugs for a single administration dosage, the solid drugs being discharged from the hopper; a movement mechanism that moves the inspection container; and an imaging device that captures an image of the solid drugs in the inspection container. As a result that the inspection device inspects the solid drugs by which the imaging device captures the image of the solid drugs in the inspection container, when number of the solid drugs is different from the prescription data, the solid drugs are disposed of, and when the number of the solid drugs is same as the prescription data, the solid drugs are packaged by the packaging device.

The drug supply device of a second aspect of the present invention is characterized in that, in the first aspect, the movement mechanism has an introduction position at which the solid drugs are discharged from the hopper into the inspection container, an imaging position at which an image of the solid drugs in the inspection container is captured by the imaging device, a disposal position at which the solid drugs are disposed of, and a filling position at which the solid drugs are discharged into the packaging device.

The drug supply device of a third aspect of the present invention is characterized in that, in the second aspect, the movement mechanism is formed by a turntable and an electric operation mechanism that rotatably supports the turntable, and the turntable includes the plurality of inspection containers on an upper surface of the turntable.

The drug supply device of a fourth aspect of the present invention is characterized in that, in the second and third aspects, the disposal position is arranged at a position that is opposite to the imaging position with respect to the introduction position.

The drug supply device of a fifth aspect of the present invention is characterized in that, in one of the second to fourth aspects, as a result of capturing an image of and inspecting the solid drugs in the inspection container using the imaging device, when the number of the solid drugs is different from the prescription data, the drug supply device moves the inspection container to the disposal position and disposes of the solid drugs at the disposal position. After that, the drug supply device moves the inspection container to the introduction position, once more discharges the solid drugs based on the prescription data from the tablet cases, and discharges the newly discharged solid drugs from the hopper into the inspection container.

A drug supply device of a sixth aspect of the present invention is characterized by providing a solid drug supply device that includes: a plurality of tablet cases in which solid drugs are stored while being categorized by type; a hopper that collects solid drugs discharged from the tablet cases on the basis of predetermined prescription data; an inspection device that inspects the solid drugs discharged by the hopper; and a packaging device that fills and packages the solid drugs inspected by the inspection device into a packaging sheet, wherein an inspection device is arranged in a pathway through which the solid drugs are conveyed from the tablet cases to the packaging device, the inspection device includes a turntable, and the turntable includes an inspection container into which the solid drugs discharged from the tablet cases are introduced. The turntable is configured to be rotated by an electric operation mechanism to a solid drug introduction position at which the solid drugs are introduced from the hopper into the inspection container, an imaging position at which an image of the solid drugs in the inspection container is captured by an imaging device, a filling position at which the solid drugs in the inspection container can move toward the packaging device, and a disposal position at which the solid drugs are disposed of from inside the inspection container. The inspection container receives the solid drugs from the hopper at the solid drug introduction position and moves to the imaging position, and when it is determined that the number of the solid drugs is as specified by the prescription data on the basis of the imaging performed by the imaging device, the inspection container is moved to the filling position. On the other hand, when it is determined that the number of the solid drugs is not as specified by the prescription data on the basis of the imaging, the inspection container is moved to the disposal position, and after the solid drugs are disposed of at that position, the inspection container is moved to the solid drug introduction position, the inspection container newly receives the solid drugs from the hopper at the solid drug introduction position and moves to the imaging position, and based on another determination as to whether or not the number of the solid drugs is as specified by the prescription data made on the basis of the imaging performed by the imaging device, the inspection container is moved to either the filling position or the disposal position in the same manner as described above.

A seventh aspect of the present invention is a drug inspection method in a drug supply device, the method performing a process in a solid drug supply device that includes a plurality of tablet cases in which solid drugs are stored while being categorized by type and a packaging device that fills and packages the solid drugs discharged from the table cases on the basis of desired prescription data into a packaging sheet, wherein: an imaging step of capturing an image of the solid drugs in a state in which the solid drugs discharged from the tablet cases are received is included at a stage before the solid drugs discharged from the tablet cases on the basis of the desired prescription data are delivered to the packaging device; based on the imaging, when it is determined that the number of the solid drugs is as specified by the prescription data, the solid drugs are moved to a filling step at which the solid drugs can be delivered to the packaging device; based on the imaging, when it is determined that the number of the solid drugs is not as specified by the prescription data, the solid drugs are moved to a disposal step at which the solid drugs are disposed of; and when the solid drugs are disposed of, a correct number of the solid drugs are caused to be once more discharged from the tablet cases and capturing an image of the solid drugs being once more discharged from the tablet cases is conducted at the imaging step again.

Advantageous Effects of Invention

In the first aspect of the invention, as a result of capturing an image of and inspecting the solid drugs using the inspection device at a stage before the solid drugs are filled into the packaging sheet, a bottle or the like, when it is determined that the number of the solid drugs is different from the prescription data, the solid drugs are disposed of. Therefore, it becomes possible to supply the drugs accurately on the basis of the prescription data.

In the second aspect of the invention, as the inspection container is moved by the movement mechanism to the introduction position, the imaging position, the disposal position, and the filling position, the movement mechanism causing the inspection container to move, it is possible to reliably perform operations of introducing the solid drugs into the inspection container and of capturing an image of the solid drugs and also operations of disposing of the solid drugs, when it is determined that the number of the solid drugs is different from the prescription data as a result of the inspection, and of discharging the solid drugs into the packaging device, when it is determined that the number of the solid drugs is same as the prescription data as a result of the inspection.

In the third aspect of the invention, as the plurality of the inspection containers arranged on the turntable are moved by the rotation of the turntable to the solid drug introduction position, the imaging position, the disposal position, and the filling position, it is possible to reliably perform operations of introducing the solid drugs into the inspection container and of capturing an image of the solid drugs and also operations of disposing of the solid drugs, when it is determined that the number of the solid drugs is different from the prescription data as a result of the inspection, and of discharging the solid drugs into the packaging device, when it is determined that the number of the solid drugs is same as the prescription data as a result of the inspection.

In the fourth aspect of the invention, according to the second and third aspects, as the disposal position is arranged at the position opposite to the imaging position with respect to the introduction position, by rotating the turntable in the normal and reverse directions, it is possible to shorten an operational time required for the inspection container to be moved to the solid drug introduction position, the imaging position, the disposal position, and the filling position, and to swiftly perform supply of drugs in a case in which an inspection device is provided.

In the fifth aspect of the invention, as the inspection container, from which the solid drugs have been disposed of once, is inspected again after the solid drugs discharged from the tablet cases on the basis of the prescription data are newly introduced thereinto, it is possible to establish an automatic control in which, even when-the inspection result is different from the prescription data, the inspection can be continuously performed and subsequently packaging can be performed by the packaging device.

In the sixth aspect of the invention, as it is possible to arrange the solid drug introduction position, the imaging position, the filling position, and the disposal position on the turntable as required, it is suitable to downsize the solid drug supply device in consideration of positional relationships with respective mechanisms installed in the solid drug supply device.

In the seventh aspect of the invention, an image of the solid drugs is captured at the stage before the solid drugs are separately packaged into the divided packaging sheet, and when it is determined based on the imaging that the number of the solid drugs is not as specified by the prescription data, the solid drugs are disposed of, then, the correct number of the solid drugs is once more discharged from the tablet cases, an image of the solid drugs is captured, and the solid drugs are inspected again. Therefore, at a stage of separately packaging the solid drugs into the divided packaging sheet, the solid drugs are always packaged on the basis of the prescription data. As a result, only the correct number of the solid drugs is packaged and it is possible to inhibit wasteful packaging.

DESCRIPTION OF EMBODIMENTS

The present invention provides a drug supply device that includes a plurality of tablet cases in which solid drugs are stored while being categorized by type and a packaging device that fills and packages the solid drugs discharged from the tablet cases into a packaging sheet, on the basis of desired prescription data. The drug supply device performs a process wherein: an imaging step of capturing an image of the solid drugs in a state in which the solid drugs discharged from the tablet cases are received is included at a stage before the solid drugs discharged from the tablet cases on the basis of the desired prescription data are separately packaged into a packaging sheet; based on the imaging, when it is determined that the number of the solid drugs is as specified by the prescription data, the solid drugs are moved to a filling step at which the solid drugs can be delivered to the packaging device; based on the imaging, when it is determined that the number of the solid drugs is not as specified by the prescription data, the solid drugs are moved to a disposal step at which the solid drugs are disposed of; and when the solid drugs are disposed of, a correct number of the solid drugs are caused to be once more discharged from the tablet cases and capturing an image of the solid drugs being once more discharged from the tablet cases is conducted at the imaging step again. Embodiments of the drug supply device will be described below.

First Embodiment

A drug supply device according to the present invention is installed in a hospital, a pharmacy or the like and is designed for filling prescribed solid drugs (solid drugs refers to all solidified drug products including tablets, capsules, pills, and lozenges, and hereinafter referred to as drugs TB) into a packaging sheet, a bottle, or the like. In an embodiment that will be described below, a solid drug supply device, which fills the solid drugs into a small sachet formed of a band-shaped packaging sheet, will be described with reference to the drawings.

Figure 1:
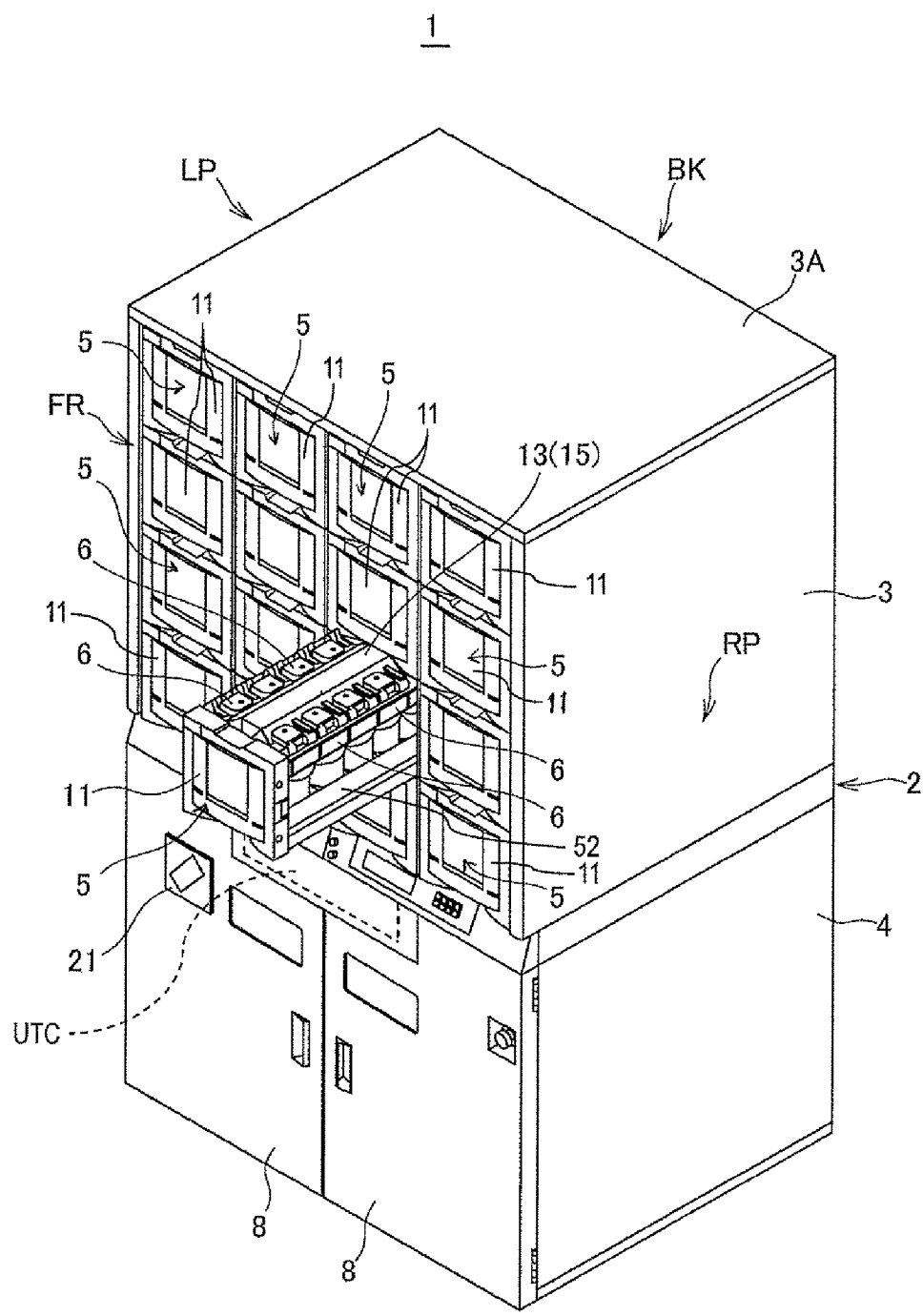
FIG. 1 is a front perspective view of a drug supply device according to an embodiment of the present invention.
Figure 2:
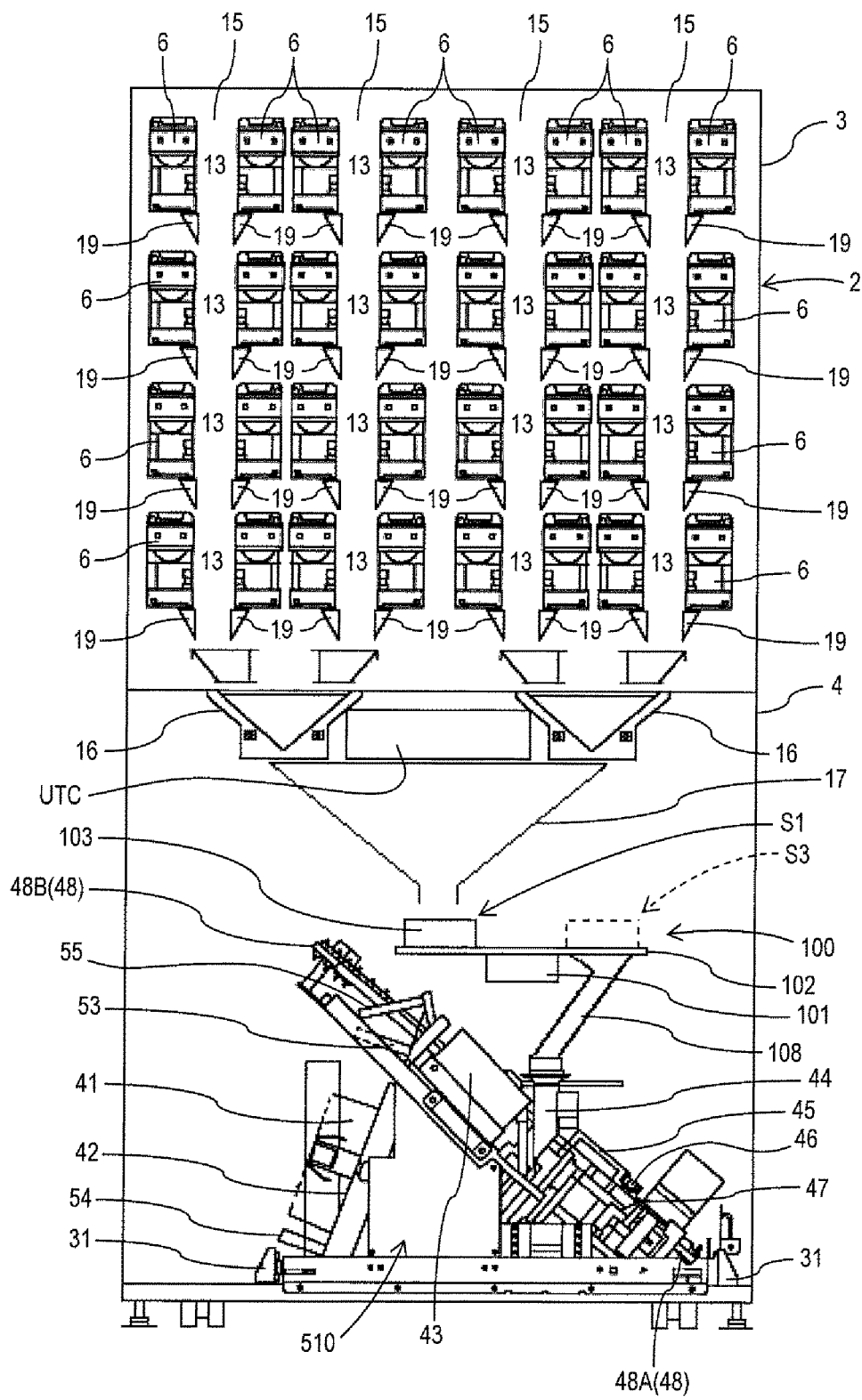
FIG. 2 is a front view showing an internal structure of the drug supply device according to the present invention.

FIG. 1 is a perspective view of a drug supply device 1 according to an embodiment of the present invention, and FIG. 2 shows an internal structure thereof. Note that in FIG. 1, a front side (front surface) of the drug supply device 1 is indicated by reference characters FR, a back side thereof is indicated by reference characters BK, a right side thereof is indicated by reference characters RP, and a left side thereof is indicated by reference characters LP. The drug supply device 1 is installed in a hospital, a pharmacy or the like. The drug supply device 1 includes tablet cases 6 (refer to FIG. 1 and FIG. 2) that are respectively provided for each type of the drugs TB (the above-described solid drugs including tablets, capsules, etc.). The drug supply device 1 discharges the drugs TB from the tablet cases 6 one by one according to types and quantities of the drugs TB specified by a prescription, collects the drugs TB at one location using a hopper 17 (refer to FIG. 2) via chutes 15 (refer to FIG. 2), which function as pathways that cause the drugs TB to fall naturally using the weight of the drugs TB, and then packages the drugs TB into a packaging sheet (sheet) S. The drug supply device 1 performs all the above-described operations, ranging from the extraction of the drugs TB to the packaging of the drugs TB, using a series of mechanisms in a fully automated manner.

As shown in FIG. 1, the drug supply device 1 includes a main body (case) 2 having a vertically long rectangular shape and a personal computer (hereinafter referred to as a PC) for controlling the drug supply device 1, the personal computer being described below. The main body 2 includes an upper structural member 3 and a lower structural member 4, which can be separated from each other, and has a structure in which the upper structural member 3 is connected on top of the lower structural member 4. The upper structural member 3 functions as a drug storage portion that stores the plurality of tablet cases 6, in which the drugs TB are contained, and an upper surface thereof is covered by a removable top panel 3A.

The upper structural member 3 is provided with a plurality of shelves 5 that form drawers of multiple rows and multiple layers, namely, four rows from right to left and four layers from top to bottom (16 shelves in total). In the shelf 5, two rows are arranged side by side, each of the rows being mounted with the plurality of tablet cases 6 in the front-to-back direction. The above-described shelves 5 are detachably screwed to sliding plate portions 27A provided on a pair of left and right drawer rails 27, the drawer rails 27 being mounted on the upper structural member 3 (refer to FIG. 3 and FIG. 4). As a result, the shelves 5 and the plurality of tablet cases 6 mounted thereon are stored in the upper structural member 3 so that they can be freely pulled out. Further, in a state of being pulled out, the shelves 5 and the tablet cases 6 are removable from the drawer rails 27 and are formed so that they can be removed toward the front side of the drug supply device 1. A door panel 11 is mounted on a front end (front side) of each of the shelves 5, and in a state in which all the shelves 5 are stored inside the upper structural member 3, each of the door panels 11 closes an opening provided on the front side of the upper structural member 3.

The shelf 5 has a structure in which the plurality of tablet cases 6 are arranged in two rows side by side. Therefore, drive bases 52 that respectively drive the tablet cases 6 are also arranged in two rows side by side. Each of the shelves 5 has a pathway 13 that is located between the two rows of the tablet cases 6 arranged side by side, the pathway 13 having open top and bottom ends and extending along the shelf 5 in the depth direction.

Further, in a state in which the respective shelves 5 are stored in the upper structural member 3, the pathways 13 of the respective shelves 5 correspond to one another in the vertical direction, the shelves 5 being positioned vertically with respect to one another, and as a result, the pathways 13 form a series of drop chutes 15 that are communicated vertically. Therefore, the present embodiment has four vertical rows of the drop chutes 15 that are formed side by side in the upper structural member 3. Since the shelves 5, which can be pulled out separately from one another, are provided vertically on the plurality of layers in the upper structural member 3 as described above, when replacing the tablet cases 6, it becomes possible to do so by pulling out each of the shelves 5.

As a result, compared with a structure in which one row of the shelves 5 in the vertical direction is pulled out simultaneously, it is possible to narrow a gap that should be formed between the shelves 5 that are arranged vertically with respect to one another when replacing the tablet cases 6, and consequently, it becomes possible to increase the number of the tablet cases 6 that can be stored in a case storage portion 8. Further, since the vertically communicated drop chutes 15 are formed as a result of forming the pathways 13 in central sections of the shelves 5 in a state in which each of the vertically arranged shelves 5 are stored in the upper structural member 3, it is possible to narrow a gap between the drop chutes 15 positioned at left and right ends of the shelves 5 in comparison with a case in which the chutes 15 are formed on side portions of the shelves 5. As a result, it becomes possible to achieve downsizing by reducing open areas of upper surfaces of shutters 16, the hopper 17, etc., the shutters 16 being described below.

Figure 3:
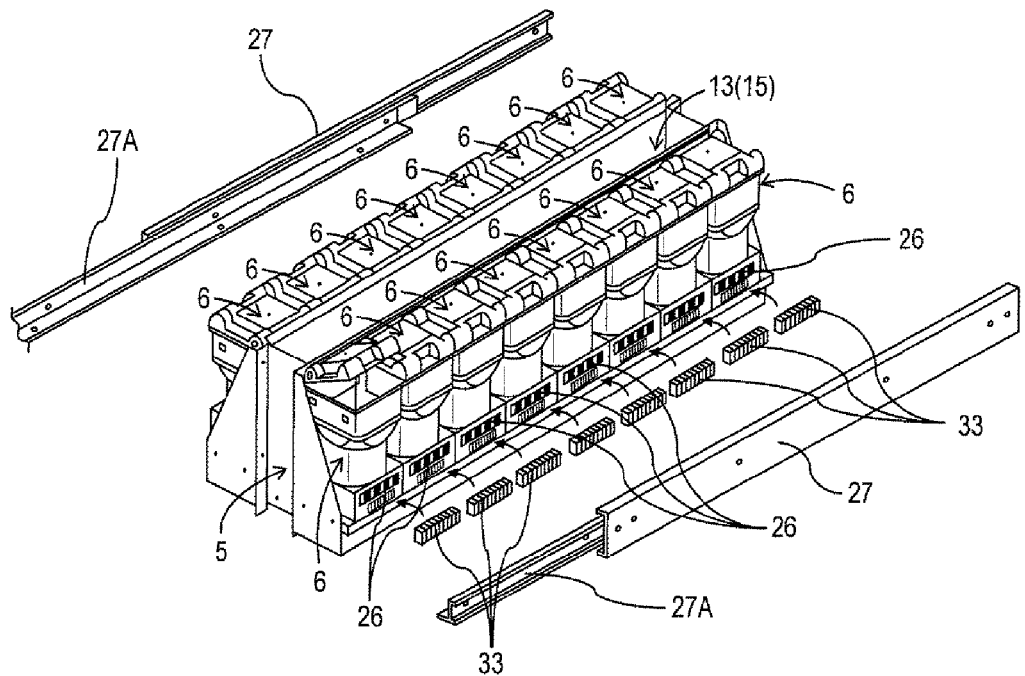
FIG. 3 is a perspective view of a shelf section in which tablet cases according to the present invention are arranged.

The tablet cases 6 are arranged on both left and right sides of the pathways 13 that are formed in the central sections of the shelves 5, and eight units of the drive bases 52, which respectively drive each of the tablet cases 6, are mounted in parallel on each side of the pathways 13 (sixteen units in total) in the front-to-back direction (FIG. 3). Note that the tablet cases 6 are connected to the drive bases 52.

Figure 4:
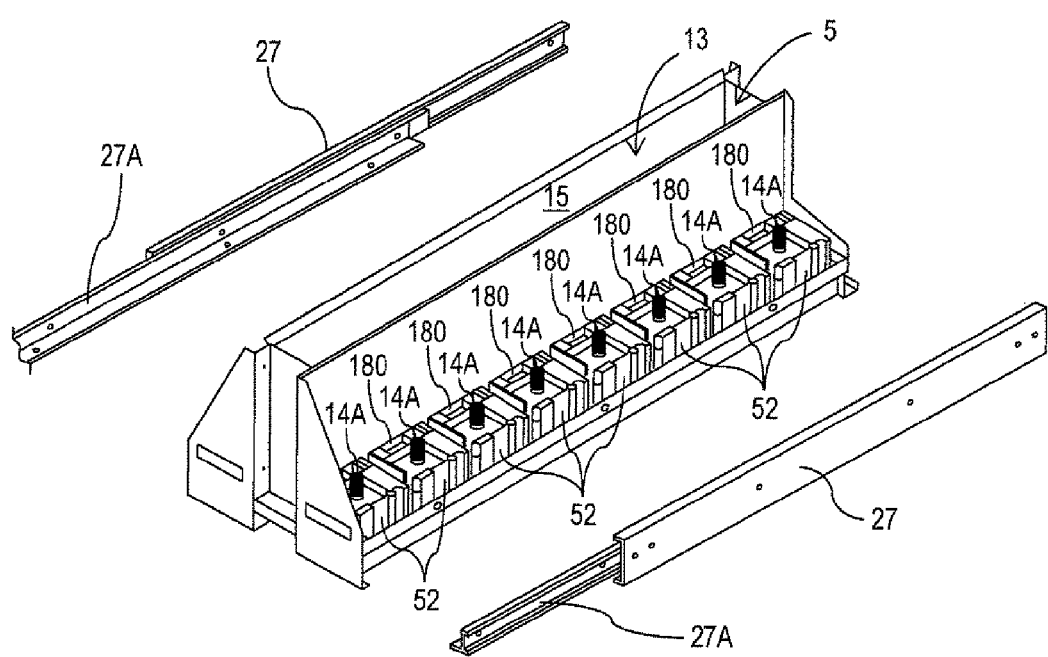
FIG. 4 is a perspective view of the shelf section in a state in which the tablet cases according to the present invention are removed.
Figure 6:
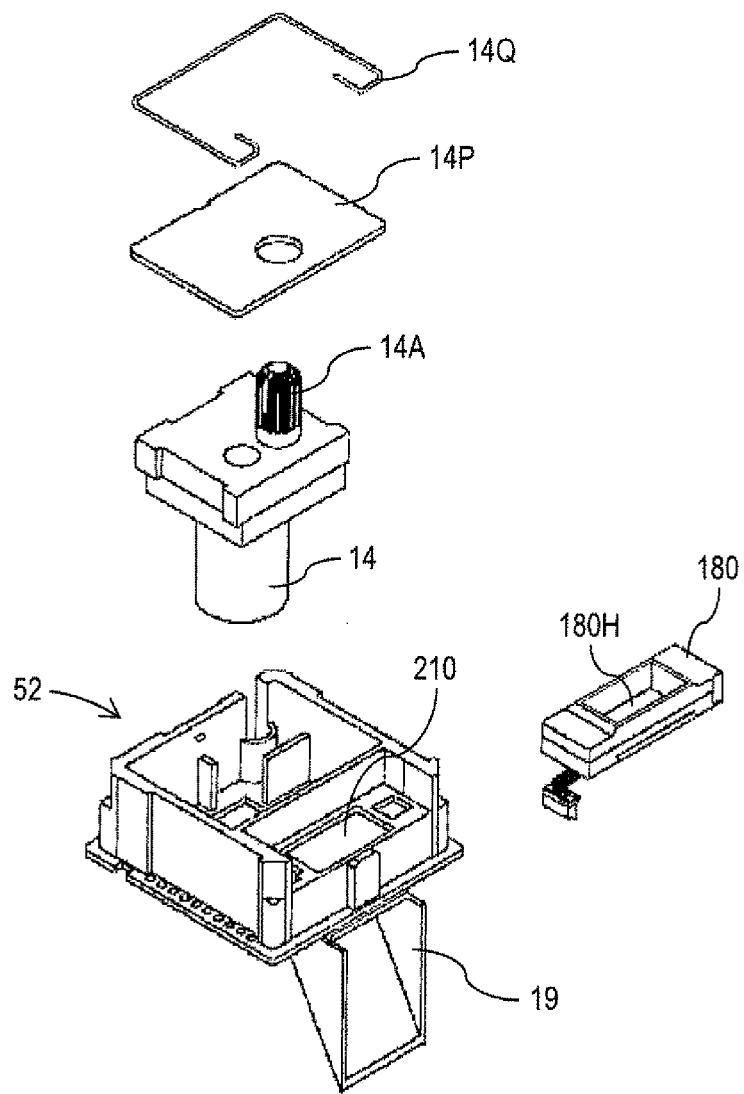
FIG. 6 is an exploded perspective view of a housing section for a drum motor of a drive base according to the present invention.

A drum motor (a drum drive motor) 14 is housed in the drive base 52 from above, and the drive motor 14 functions as a drum drive motor that is formed by a direct-current motor with a brush. The drum motor 14 is fixed to the drive base 52 by a cover 14P and a metal fitting 14Q. In this state, a drive shaft 14A of the drive motor 14 protrudes above the cover 14P (FIG. 4 and FIG. 6). Further, an optical drug detection sensor 180 that forms a through hole 180H corresponding to the discharge port 210 is mounted at a discharge port 210 that is formed in the drive base 52. In a section of the drive motor 52 located below the drug detection sensor 180, a discharge chute 19 is formed that extends diagonally downward from the discharge port 210

(FIG. 2 and FIG. 6). Then, the discharge chute 19 has a communication opening with the drop chute 15 (FIG. 2).

Figure 5:
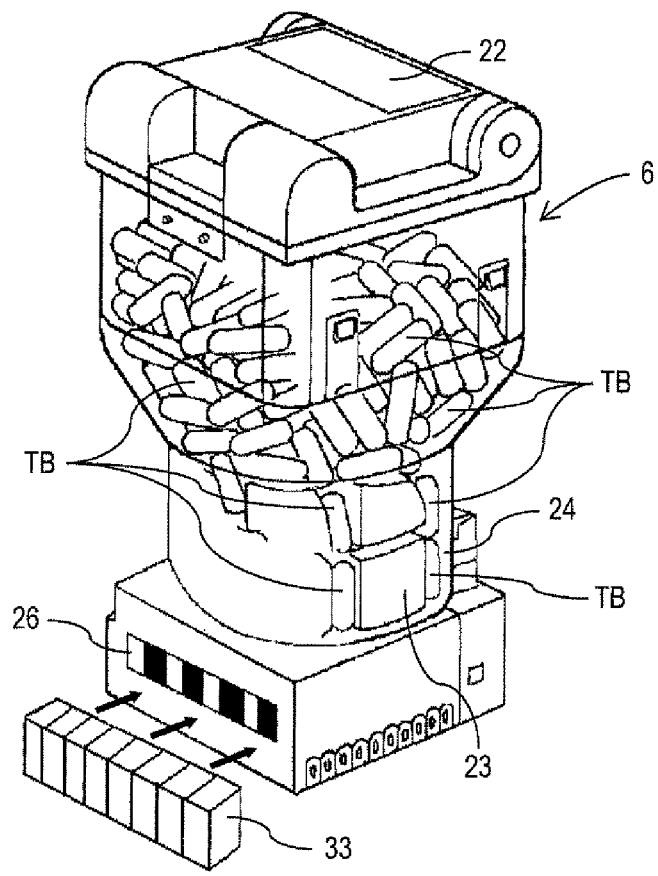
FIG. 5 is a perspective view of the tablet case according to the present invention.

Meanwhile, the tablet case 6 has an opening on an upper surface thereof, and the opening on the upper surface is closed by a lid 22 that can be opened and closed freely (FIG. 5). Further, a discharge drum 23 is mounted on an inner bottom portion of the tablet case 6, and a plurality of vertical grooves 24 are formed around a side surface of the discharge drum 23 having a predetermined interval therebetween. After opening the lid 22, the drugs TB are filled into the tablet case 6 from the opening on the upper surface thereof, and a state is obtained in which two pieces of the drugs enter into each of the vertical grooves 24 of the discharge drum 23. Further, an optically identifiable identification code (a barcode, etc.) 26 is attached to a side surface of a lower portion of the tablet case 6 that is formed into a shape to which the drive base 52 is fitted. The identification code 26 is a code for identifying types of the drugs TB that are filled into the tablet case 6.

The tablet case 6 is mounted on the above-described drive base 52 and is detachably connected thereto. In this case, the tablet case 6 is mounted so that the identification code 26 faces outward with respect to the shelf 5 (the opposite side of the pathway 13). At that time, the discharge drum 23 detachably engages with the drive shaft 14A of the drive motor 14. Then, when the drive motor 14 is driven in a normal rotational direction, the discharge drum 23 is rotated in a normal direction and the drugs TB fall into the discharge chute 19 one by one as the vertical grooves 24 of the discharge drum 23 are sequentially aligned with the discharge port 210.

The drugs TB that pass through the discharge port 210 are detected by the drug detection sensor 180. Further, the drugs TB that fall into the discharge chute 19 are discharged into the drop chutes 15. Further, when there are no longer any of the drugs TB in the tablet case 6, the tablet case 6 is removed from the drive base 52 to be refilled.

On left and right side surfaces of the shelves 5, a plurality of optical identification sensors 33 are mounted at positions corresponding to the respective tablet cases 6 of the respective shelves 5, the tablet cases 6 being positioned at left and right ends of the shelves 5 (FIG. 3). More specifically, each of the identification sensors 33 is arranged below the identification code 26 so as to correspond to each of the identification codes 26 of the tablet cases 6 positioned on the sides corresponding to the left and right side surfaces of the shelves 5. The identification sensors 33 are used to read information of the identification codes 26 in a non-contact manner.

The lower structural member 4 has open front and upper sides and is communicated with the upper structural member 3 on the upper side thereof. As shown in FIG. 2, in the lower structural member 4, a pair of the left and right shutters 16 provided below the drop chutes 15, a single unit of the hopper 17 provided below the shutters 16, and an inspection device 100, a packaging device 18, etc. provided below the hopper 17 are housed and installed. An opening on the front side of the lower structural member 4 is formed by double front doors 8, which open outward (refer to FIG. 1), and which can be opened and closed freely. A removal opening 21 is formed on the left front door 8 on the front side of the lower structural member 4. The removal opening 21 is provided for removing a divided package (a small sachet SS and a series of small sachets SS that will be described below) into which predetermined types and quantities of the drugs TB are filled, and the divided package into which the drugs TB have been filled is discharged to the removal opening 21.

As shown in FIG. 2 and FIG. 7 to FIG. 9, the left and right shutters 16 each have a wide opening on the upper side thereof and have a rectangular funnel shape that gradually narrows toward a bottom end thereof. The shutters 16 are opened and closed by a shutter solenoid 123, which will be described below, and temporarily receive the drugs TB that fall through the respective drop chutes 15 toward the hopper 17. An additional drug feeder (referred to as UTC) is provided between the shutters 16 so that the additional drug feeder can be freely pulled out toward the front. The additional drug feeder is a feeder for supplying additional drugs TB as required, and the feeder UTC is communicated with the hopper 17. The hopper 17 has a wide opening on the upper side thereof and has a rectangular funnel shape that gradually narrows toward a bottom end thereof. The hopper 17 receives the drugs TB that fall from the shutters 16 and the additional drug feeder UTC and supplies the drugs TB to the inspection device 100 provided below the hopper 17.

Figure 7:
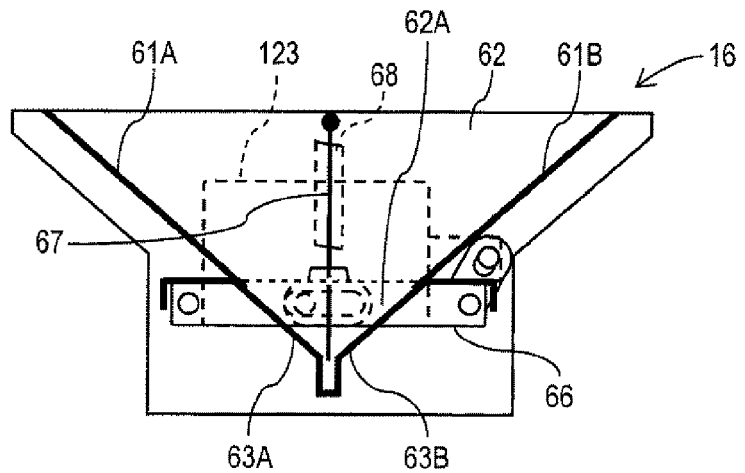
FIG. 7 is an explanatory diagram of a state in which shutters according to the present invention are closed.
Figure 8:
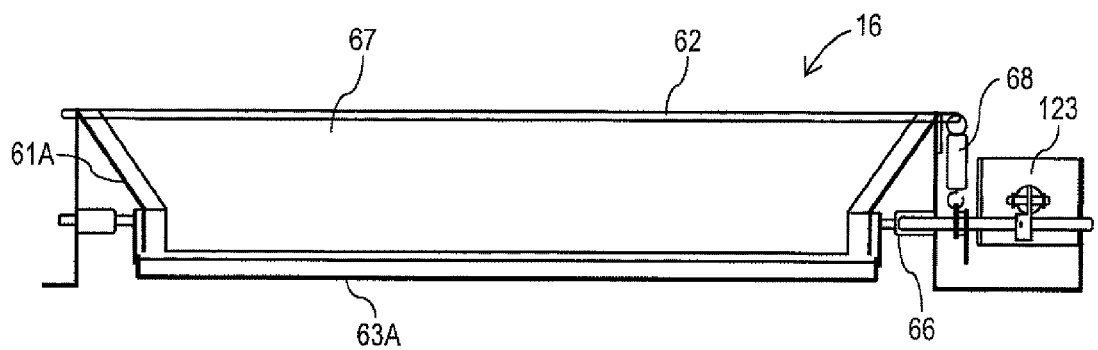
FIG. 8 is a side view of the shutters according to the present invention.
Figure 9:
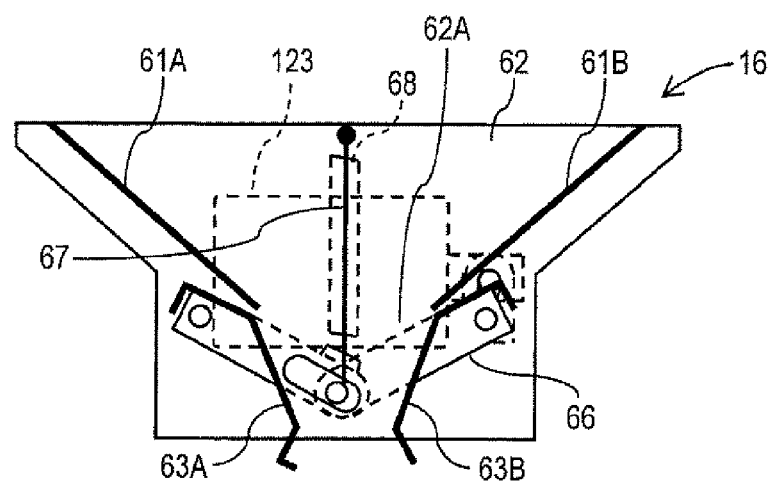
FIG. 9 is an explanatory diagram of a state in which the shutters according to the present invention are open.

Next, a structure of each of the above-described shutters 16 will be described with reference to FIG. 7 to FIG. 9. As a whole, the shutter 16 has a substantially bilaterally symmetrical shape that is longer in the depth direction of the lower structural member 4 and has left and right inclined walls 61A and 61B that are inclined from bottom to top while becoming more separated from each other. The shutter 16 is formed by a main body 62, which has a rectangular funnel shape with a widely open upper side, and a pair of opening and closing plates 63A and 63B, which open and close a narrowed bottom end opening 62A of the main body 62, etc.

The respective opening and closing plates 63A and 63B are operated by the shutter solenoid 123, a coil spring 68, and a link mechanism 66. The opening and closing plates 63A and 63B are driven to obtain a closed state as shown in FIG. 7, in which bottom ends of the respective opening and closing plates 63A and 63B mutually abut each other substantially continuously from bottom ends of the left and right inclined walls 61A and 61B, resulting in the bottom end opening 62A of the main body 62 being closed, and an open state as shown in FIG. 9, in which the bottom ends of the opening and closing plates 63A and 63B are mutually separated from each other as a result of the opening and closing plate 63A rotating in the clockwise direction in the figure and the opening and closing plate 63B rotating in the counter-clockwise direction in the figure, so that the bottom end opening 62A of the main body 62 is open.

Further, a curtain 67 is mounted in the shutter 16 as a shock-absorbing member. The curtain 67 is formed of a material, such as a thin cloth, rubber, or synthetic resin, which has sufficient flexibility to be able to absorb the kinetic energy of the drugs TB, which are dropped from the chutes 15, collide with the left and right inclined walls 61A and 61B, and bounce back from the inclined walls 61A and 61B. The curtain 67 is suspended from the center of an upper portion of the main body 62, the curtain being provided inside the main body 62, and a bottom end of the curtain 67 extends further below the bottom end opening 62A of the main body 62 and extends to a position at which the bottom end of the curtain 67 is sandwiched by the respective opening and closing plates 63A and 63B in a state in which both the opening and closing plates 63A and 63B are closed, as shown in FIG. 7.

With the above-described structure, the kinetic energy of the drugs TB, which fall into the shutters 16 and bounce up and down, is absorbed by the curtain 67, and as a result, the drugs TB are swiftly collected from the bottom end opening 62A onto the opening and closing plates 63A and 63B and come to a stop. Particularly, as the curtain 67 extends from an upper portion of the shutter 16 to the bottom end thereof, it becomes easier for the bouncing-up-and-down drugs TB to come into contact with the curtain 67, and due to the further improved shock-absorbing function, a time required for the drugs TB to come to a stop is further shortened. Further, as the curtain 67 is sandwiched by the respective opening and closing plates 63A and 63B, a noise that is generated when the bottom ends of the opening and closing plates 63A and 63B abut against each other is also absorbed.

Figure 10:
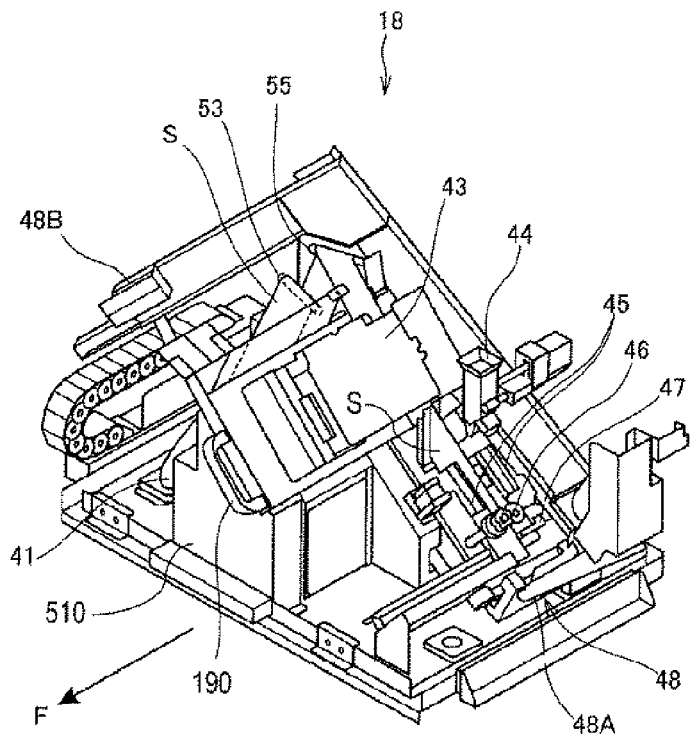
FIG. 10 is a perspective view of a packaging device according to the present invention as viewed from above and diagonally from the front right.
Figure 11:
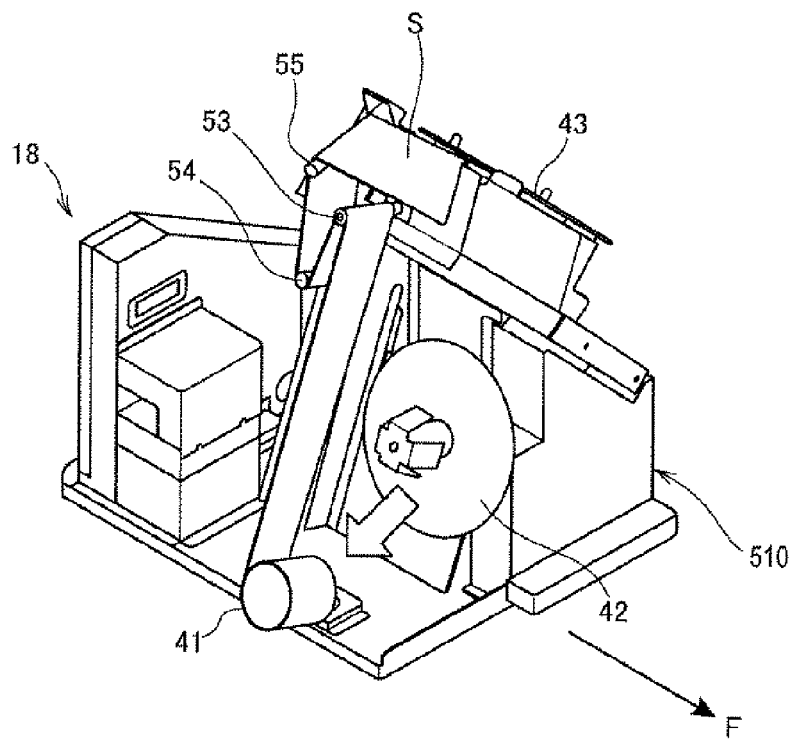
FIG. 11 is a perspective view of the packaging device according to the present invention as viewed from above and diagonally from the front left.

The packaging device for filling and packaging the drugs TB for a single administration dosage into a packaging sheet S is detachably screwed to a pair of left and right drawer rails 31 that are mounted at left and right sections of a bottom surface inside the lower structural member 4. By this, the packaging device 18 can be freely pulled out toward the front from inside the lower structural member 4 in a state in which the front doors 8 are open, and further, the packaging device 18 can be attached to and removed from the drawer rails 31 in a state of being pulled out. FIG. 10 is a perspective view of the packaging device 18 as viewed from above and diagonally from the front right, and FIG. 11 is a perspective view of the drug supply device 1 as viewed from above and diagonally from the front left. Note that an arrow indicated by a reference character F in FIG. 10 indicates a direction in which the packaging device 18 is pulled out when the packaging device 18 is pulled out toward the front side of the drug supply device 1, and a reference numeral 190 indicates a handle used for pulling out the packaging device 18.

An embodiment that will be described below shows a case in which the packaging device 18 is formed to fill and package the drugs TB for a single administration dosage into the packaging sheet S. As shown in FIG. 10 and FIG. 11, the packaging device 18 includes: a sheet feeding board 42 on which a roll 41 is detachably mounted, a heat sealable packaging sheet S being wound around the roll 41; a printer unit 43 that functions as a printing portion for printing graphics such as characters and barcodes on the packaging sheet S; a nozzle 44 that functions as a drug filling portion for filling the drugs TB into the packaging sheet S; a heat sealing head 45 that functions as a packaging portion for closing the packaging sheet S by heat sealing, the packaging paper S being filled with the drugs; a feed roller 46 that forms a conveyance mechanism for conveying the packaging sheet S pulled out from the roll 41; a cutter 47 that cuts the packaging sheet S; and a conveyor unit 48 that conveys the packaging sheet S (the divided package) to the removal opening 21, the packaging paper S packaging the drugs TB. The sheet feeding board 42, the printer unit 43, the nozzle 44, the heat sealing head 45, the feed roller 46, the cutter 47, and the conveyor unit 48 are arranged along a conveyance pathway of the packaging sheet S, in the above-mentioned order from the upstream side of the pathway. Note that FIG. 11 shows a state in which the roll 41 is removed from the sheet feeding board 42.

The packaging device 18 includes a box body 510 that is vertically arranged upward from the center of the bottom surface in the left-and-right direction inside the lower structural member 4. Inside the box body 510, parts that are not exposed outside the packaging device 18 (a drive motor for the heat sealing head 45, a drive mechanism of a movable roller 54 that will be described below, etc.) are arranged, and members that are exposed outside the packaging device 18 are arranged using spaces available beside, above, and below the box body 510.

More specifically, the sheet feeding board 42, a first conveyance roller 53, which guides the packaging sheet S that has been pulled out diagonally upward and to the left from the roll 41 of the sheet feeding board 42 to the frontmost tip and folds the packaging sheet S in the downward direction, a movable roller 54, which applies tension to the packaging sheet S on a downstream side of the first conveyance roller 53, and a second conveyance roller 55 that guides the packaging sheet S on a downstream side of the movable roller 54 and folds the packaging sheet S in the direction toward an inlet port of the printer unit 43 are arranged to the left of the box body 510, as shown in FIG. 2 and FIG. 11. By using these, the conveyance pathway is formed through which the packaging sheet S is conveyed to the printer unit 43 while tension is applied to the packaging sheet S.

The first conveyance roller 53 is fixed above the roll 41 mounted on the sheet feeding board 42, so that it is easy for an operator (user) to wind the packaging sheet S that has been pulled out from the roll 41 when replacing the roll 41. Further, rotating axes of the first conveyance roller 53, the movable roller 54, and the roller 41 mounted on the sheet feeding board 42 are all parallel to one another and extend diagonally upward and to the left. On the other hand, the second conveyance roller 55 is not parallel to the above. Note that, as long as the rotating axes of the first conveyance roller 53, the movable roller 54, and the roll 41 mounted on the sheet feeding board 42 are parallel to one another and can be arranged in the space located on the left side of the box body 510, the rotating axes may be changed as required and a position of the second conveyance roller 55 can also be changed as required.

As shown in FIG. 2 and FIG. 10, on an upper surface of the box body 510, the printer unit 43 is arranged so that it is formed on an inclined surface inclining downward and to the right, and the packaging sheet S is conveyed through the printer unit 43 downward and to the right. A lower end of the nozzle 44, the heat sealing head 45, the feed roller 46, and the cutter 47 are arranged, in this order, to the lower right of the printer unit 43, and an upstream end 48A of the conveyor unit 48 is positioned to the right of the cutter 47. The conveyor unit 48 extends diagonally upward and to the left behind the box body 510 and then extends forward after being bent in the forward direction on the left side behind the box body 510. A rear end 48B is provided in a position that communicates with the removal opening 21 of the front doors 8 (refer to FIG. 1).

Figure 15:
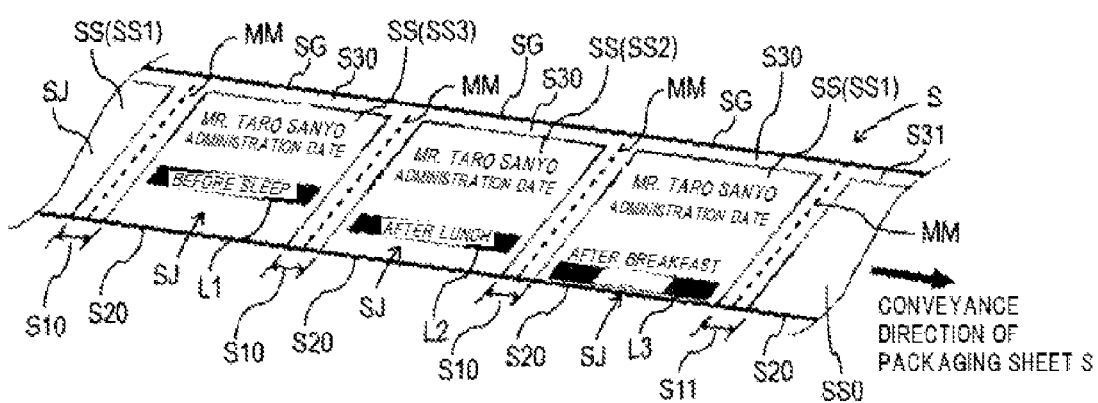
FIG. 15 is a diagram showing a printed state of a packaging sheet according to the present invention.

Next, basic operations of the packaging device 18 will be described. The roll 41 is a roll around which is wound the long packaging sheet S (also referred to as a divided packaging sheet), which is double-folded (folded in half) in advance, and the roll 41 is mounted on the sheet feeding board 42 with the axis of the roll 41 being positioned diagonally downward and to the right with respect to the horizontal surface (refer to FIG. 2). In a stand-by mode that is obtained before performing a normal drug filling operation, while being conveyed by the feed roller 46, the packaging sheet S passes through the first conveyance roller 53, the movable roller 54, and the second conveyance roller 55 in this order, and thus passes through the printer unit 43. Then, after an open side of the double-folded packaging sheet S is expanded and forms a V-shaped cross section with a bottom portion S20, the packaging sheet S passes through the nozzle 44 and reaches the heat sealing head 45. At this point, the packaging sheet S is pinched by the heat sealing head 45, and as shown in FIG. 15, stands by in a state in which a section S31 (the same as a section S30 described below) and a section S11 (the same as a section S10 described below) have been heat sealed. In order to control timings of printing and drug filling into the small sachet SS, as described below, a number of times (units) that the heat sealing is applied to the sections S31 and S11 can be formed at a plurality of locations instead of at one location, so that a plurality of so-called empty small sachets SS (a section indicated by SS0 in FIG. 15) are obtained. In this state, as shown in FIG. 15, the small sachet corresponding to a section on which "After Breakfast" is printed (a section indicated by SS1) is formed by a section of the bottom portion S20 and the heat sealing portion S11 in the form of a substantially triangular-shaped drug storage portion, which forms an opening SG used for filling the drugs TB. In this state, by starting the normal drug filling operation, the packaging sheet S is conveyed by the feed roller 46 and passes through the first conveyance roller 53, the movable roller 54, and the second conveyance roller 55 in this order before being conveyed to the printer unit 43. Then, prescription information (a patient name, an administration date, an administration period, etc. indicated by reference characters SJ corresponding to the characters "After Breakfast" in FIG. 15) is printed on a surface of the packaging sheet S by the printer unit 43 in conjunction with the drug filling operation.

After the printing process, the open side of the double-folded packaging sheet S is expanded so that the packaging sheet S (also referred to as the divided packaging sheet) has the V-shaped cross section. Then, the packaging sheet S is conveyed diagonally downward as described above, and after the predetermined drugs TB are filled into the small sachet SS (the section indicated by SS1) from the V-shaped opening SG through the nozzle 44, the sections S10 and S30 shown in FIG. 15 are sealed by heat in a state in which the conveyed packaging sheet S is pinched by the heat sealing head 45 from both sides. As a result, the small sachet SS (the section indicated by SS1) is formed, inside which a single packaging portion of the drugs TB of a prescribed size is sealed, and at the same time, the small sachet SS, which functions as a next drug filling portion (a section indicated by SS2), is formed in the form of the substantially triangular-shaped drug storage portion that forms the opening SG. In this manner, sequentially, the small sachet SS of a single packaging portion corresponding to "After Lunch" (the section indicated by SS2) and the small sachet SS of a single packaging portion corresponding to "Before Sleep" (a section indicated by SS3) are formed in sequence. In this manner, the small sachet SS corresponding to "After Breakfast" (the section indicated by SS1), the small sachet SS corresponding to "After Lunch (the section indicated by SS2), and the small sachet SS corresponding to "Before Sleep" (the section indicated by SS3) are sequentially formed for the number of units corresponding to the number of administration dates (refer to FIG. 15), and those sachets are guided to the removal opening 21. Note that, although a vertically perforated separating portion MM (refer to FIG. 15) is formed in a central section of a heat healing portion S10 (including S11) in order to make it easy for a patient to separate each of the small sachets SS when the patient takes the drugs TB, the separating portion MM is formed, at the same time as the heat sealing portion S10 is formed, by a teeth body (not shown in the figures) which is attached to the heat sealing head 45 that forms the heat sealing portion S10, the teeth body forming a plurality of needle-shaped protrusions.

Figure 12:
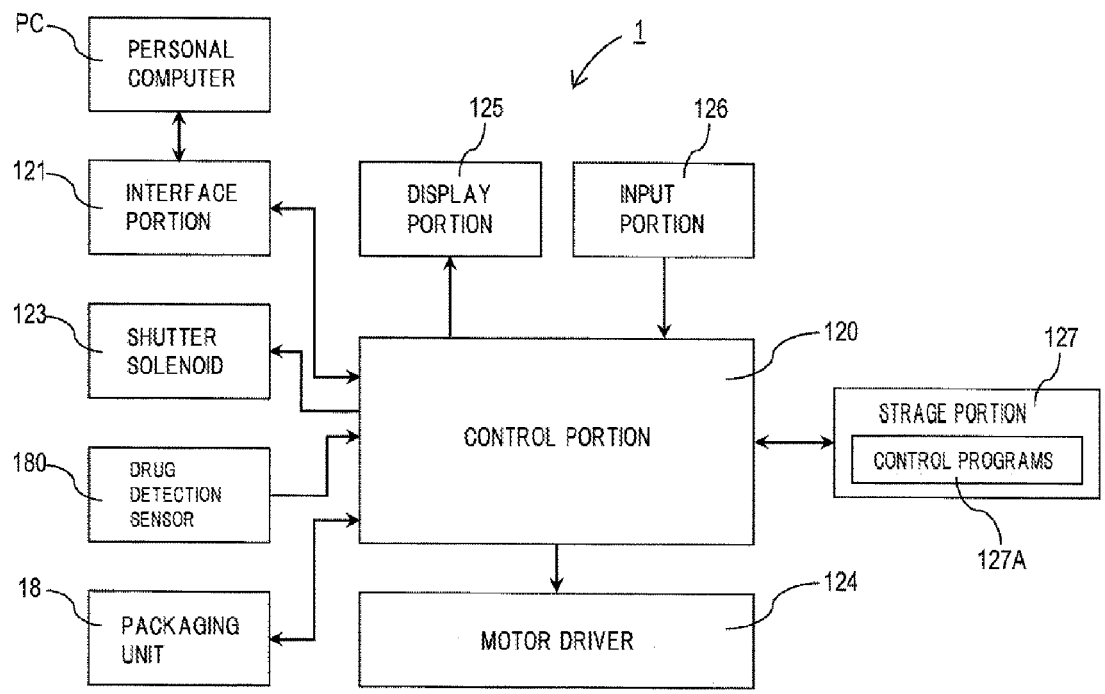
FIG. 12 is a block diagram of a functional configuration of the drug supply device according to the present invention.

FIG. 12 is a block diagram showing a functional configuration of the drug supply device 1. A control portion 120 centrally controls each portion of the drug supply device 1 using a microcomputer control method and includes a CPU (Central Processing Unit) as operation execution means, a ROM (Read Only Memory) that stores basic control programs that are executed by the CPU, data relating to the basic control programs, etc. in a non-volatile manner, a RAM (Random Access Memory) that temporarily stores the programs executed by the CPU and the data relating to the programs, etc., and other peripheral circuits, etc. Further, the control portion 120 performs various timing operations and supervision of the current time on the basis of a standard clock generated by an oscillator that is not shown in the figures. The packaging device 18, an interface portion 121, the drug detection sensor 180, the shutter solenoid 123, a motor driver 124, a display portion 125, an input portion 126, and a storage portion 127 are connected to the control portion 120.

Under the control of the control portion 120, as described above, the packaging device 18 creates the divided package filled with the predetermined drugs and also conveys the created divided package to the removal opening 21 using the conveyor unit 48. The interface portion 121 is connected to the PC via a signal communication cable, etc. and transmits and receives various signals to and from the PC under the control of the control portion 120. With this structure, various signals can be transmitted and received between the PC and the drug supply device 1, and also, the operator (user) can give various instructions to the drug supply device 1 via the PC.

The drug detection sensor 180 detects the drugs discharged from the tablet cases 6 and outputs a detected value to the control portion 120. The control portion 120 counts the number of the drugs discharged from the tablet cases 6 on the basis of the detection value input from the drug detection sensor 180. The shutter solenoid 123 operates the opening and closing plates 63A and 63B of the shutters 16 under the control of the control portion 120. The motor driver 124 is connected to the packaging device 18 and various motors provided in an electric operation mechanism 101, which will be described below, and under the control of the control portion 120, the motor driver 124 supplies a drive current to the above-described motors and controls driving of the motors.

The display portion 125 displays various information under the control of the control portion 120. Based on an input operation by the operator, the input portion 126 outputs the operator's input to the control portion 120. The storage portion 127 is formed by an EEPROM, a flash memory or the like, and stores various data in a rewritable manner under the control of the control portion 120. A control program 127A, etc., which are executed by the control portion 120, are stored in the storage portion 127.

The present invention is provided with the inspection device 100 so that the drugs TB are always packaged as specified by the prescription data at a stage at which the drugs TB are separately packaged into the divided packaging sheet S. According to the present invention, an image of the drugs TB discharged from the tablet cases 6 is captured at a stage before the drugs TB are separately packaged into the divided packaging sheet S by the packaging device 18, and based on the imaging, it is checked that the number of the drugs TB is same as the number of the solid drugs specified by the prescription data. Then, based on the inspection, when it is determined that the number of the drugs TB is not as specified by the prescription data, the drugs TB are disposed of and then a correct number of the drugs TB is once more discharged from the tablet cases. Then, an image of the drugs TB is again captured to check that the number of the drugs TB is same as the number specified by the prescription data, and when the number of the drugs TB is as specified by the prescription data, the divided packaging sheet S is guided to the packaging device 18.

Therefore, with the above-described structure, the drug supply device 1 is started up through an operation of the PC, and the number of the drugs TB required for a single packaging portion (a single administration dosage), which is taken at each administration period, such as "Morning", "Noon", and "Night", is discharged from the respective tablet cases 6 through an operation of the control portion 120. After the drugs TB are received by the shutters 16, the opening and closing plates 63A and 63B are opened by energization of the shutter solenoid 123, the number of the drugs TB for the single packaging portion (the single administration dosage) is supplied to the hopper 17 and introduced to the inspection device 100. Therefore, at a stage before separately packaging the single packaging portion (the single administration dosage) of the drugs TB, which are discharged from the tablet cases 6 into the small sachet SS of the divided packaging sheet on the basis of desired prescription data, the inspection device 100 of the present invention performs an introduction step of introducing the drugs TB for the single packaging portion discharged from the tablet cases 6 to an inspection container 103, an imaging step of capturing an image of the drugs TB, which are in a state of being received by the inspection container 103, a filling step at which it is possible to fill the drugs TB into the packaging sheet S using the packaging device 18 when the imaging determines that the number of the solid drugs is as specified by the prescription data, and a disposal step at which the drugs TB are disposed of when the imaging determines that the number of the solid drugs is not as specified by the prescription data. Further, when the drugs TB are disposed of in the disposal step, the correct number of the drugs TB for the single packaging portion is once more discharged from the tablet cases 6, and by once more performing a process of newly capturing an image of the drugs TB discharged from the tablet cases 6 at the above-described imaging step, the inspection device 100 performs either an operation of advancing to the above-described filling step or an operation of advancing to the above-described disposal step.

Figure 13:
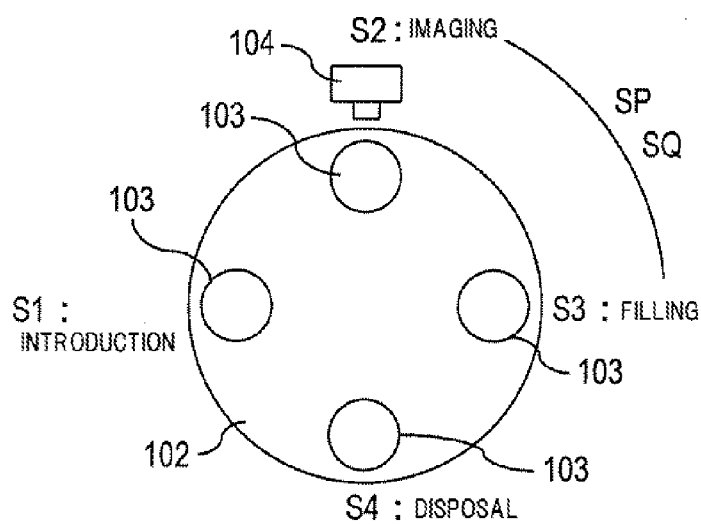
FIG. 13 is a plan view illustrating positions of inspection containers placed on a turntable of an inspection device according to the present invention and printing and packaging steps thereof.

Therefore, as one embodiment, the inspection device 100 is provided so that the inspection is carried out before the drugs TB, which are received by the hopper 17, are discharged (supplied) to the packaging device 18. As shown in FIG. 13, as a movement mechanism, the inspection device 100 includes a turntable 102 that is supported by the electric operation mechanism 101 in a manner in which the turntable 102 can rotate in normal and reverse directions. Further, the inspection device 100 includes the inspection container 103, to which the drugs TB for the single packaging portion (the single administration dosage) are introduced from the hopper 17, on the turntable 102 that is supported to be substantially horizontal. In the normal direction (the direction of right turning) from a solid drug introduction position S1, at which the drugs TB are introduced from the hopper 17, an imaging position S2 at which an image of the drugs TB in the inspection container 103 is captured by an imaging device and a filling position S3 at which the drugs TB in the inspection container 103 can move to the packaging device 18 are sequentially arranged, and a disposal position S4, at which the drugs TB are disposed of from inside the inspection container 103, is arranged in the reverse direction (the direction of left turning) from the solid drug introduction position S1. In order to perform the operations sequentially, the inspection containers 103 are arranged on the turntable 102 at respective positions corresponding to the solid drug introduction position S1, the imaging position S2, the filling position S3, and the disposal position S4, and in the embodiment as shown in FIG. 13, the solid drug introduction position S1, the imaging position S2, the filling position S3, and the disposal position S4 are arranged with substantially equal intervals therebetween.

Then, after receiving the drugs TB into the inspection container 103 from the hopper 17 at the solid drug introduction position S1, the inspection device 100 moves the inspection container 103 to the imaging position S2 by rotating the turntable 102 in the normal direction using the electric operation mechanism 101 on the basis of the operation of the control portion 120. Then, based on the operation of the control portion 120, when it is determined that the number of the solid drugs is as specified by the prescription data on the basis of the imaging performed by an imaging device 104 that is formed by a CCD camera or the like that can capture a color image, the inspection device 100 moves the inspection container 103 to the filling position S3 by rotating the turntable 102 in the normal direction using the electric operation mechanism 101 formed by a motor. On the other hand, based on the operation of the control portion 120, when it is determined that the number of the solid drugs is not as specified by the prescription data on the basis of the imaging performed by the imaging device 104, after moving the inspection container 103 to the disposal position S4 by rotating the turntable 102 in the reverse direction using the electric operation mechanism 101 and disposing of the drugs TB, the inspection device 100 moves the inspection container 103 to the solid drug introduction position S1 by rotating the turntable 102 in the normal direction using the electric operation mechanism 101 on the basis of the operation of the control portion 120, causes the inspection container 103 to newly receive the drugs TB from the hopper 17 at the solid drug introduction position S1, moves the inspection container 103 to the imaging position S2 in the same manner as described above, and then moves the inspection container 103 to either the filling position S3 or the disposal position S4 in the same manner as described above on the basis of the determination on whether the number of the solid drugs is as specified by the prescription data or not, the determination being made on the basis of the imaging performed by the imaging device 104 in the same manner as described above. Note that, when the inspection container 103 is moved from the imaging position S2 to the disposal position S4, the turntable 102 may be rotated in the normal direction. In this case, the electric operation mechanism 101 is sufficient as long as it is rotatable in the normal direction, and further, by making the rotational direction unidirectional, a control method thereof can be simplified.

FIG. 13 illustrates positions of the inspection containers 103 on the turntable 102 of the inspection device 100 and steps of printing SP and packaging SQ. As described above, based on the operation of the control portion 120, when it is determined that the number of the solid drugs is as specified by the prescription data on the basis of the imaging performed by the imaging device 104, the inspection container 103 is moved to the filling position S3 by rotating the turntable 102 in the normal direction using the electric operation mechanism 101, and an operation is performed in which the drugs TB are filled and packaged into the packaging sheet S by the packaging device 18 that can be called a filling device.

Since it is difficult to perform printing by the printer unit 43 at a stage in which the drugs TB are already filled into the packaging sheet S as the drugs TB obstruct the printing, the printing is performed at a stage before the drugs TB are filled into the small sachet SS of the packaging sheet S. Further, as described above, in terms of an operational sequence, after the prescription information is printed on the packaging sheet S, the packaging device 18 seals a required section of the packaging sheet S by heat using the heat sealing head 45 and forms a section of the small sachet SS. Therefore, in combination with the above-described operation, when it is determined that the number of the solid drugs is as specified by the prescription data on the basis of the imaging performed by the imaging device 104, the printer unit 43 prints the prescription information on the surface of the packaging sheet S on the basis of the prescription data at the printing step SP, then subsequently, a predetermined portion of the packaging sheet S is sealed by heat at the packaging step SQ, at which the packaging paper S is pinched and sealed by heat by the heat sealing head 45, and the inspection container 103, which is moved to the filling position S3, is caused to perform an operation of filling the drugs TB into the packaging sheet S using the packaging device 18. All of those operations are illustrated in FIG. 13.

Therefore, in order to perform the printing step SP, when it is determined that the number of the solid drugs is as specified by the prescription data on the basis of the imaging performed by the imaging device 104, based on the operation of the control portion 120, the inspection container 103 is caused to stay at the imaging position S2 or the inspection container 103 is moved to the filling position S3 by rotating the turntable 102 in the normal direction using the electric operation mechanism 101 and caused to standby in that position. In this state, along with a predetermined conveyance of the packaging sheet S, the printer unit 43 prints predetermined prescription information on a predetermined surface of the packaging sheet S. After the printing, along with the predetermined conveyance of the packaging sheet S, the heat sealing head 45 seals a required position of the packaging sheet S by heat. After the heat-sealing, the inspection container 103, which is caused to stay at the imaging position S2, is moved to the filling position S3 by rotating the turntable 102 in the normal direction, and further, the inspection container 103, which is moved to the filling position S3 and caused to stand by in that position, performs an operation in that state, in which the drugs TB in the inspection container 103 are filled into the small sachet SS of the packaging sheet S by the packaging device 18.

Figure 14:
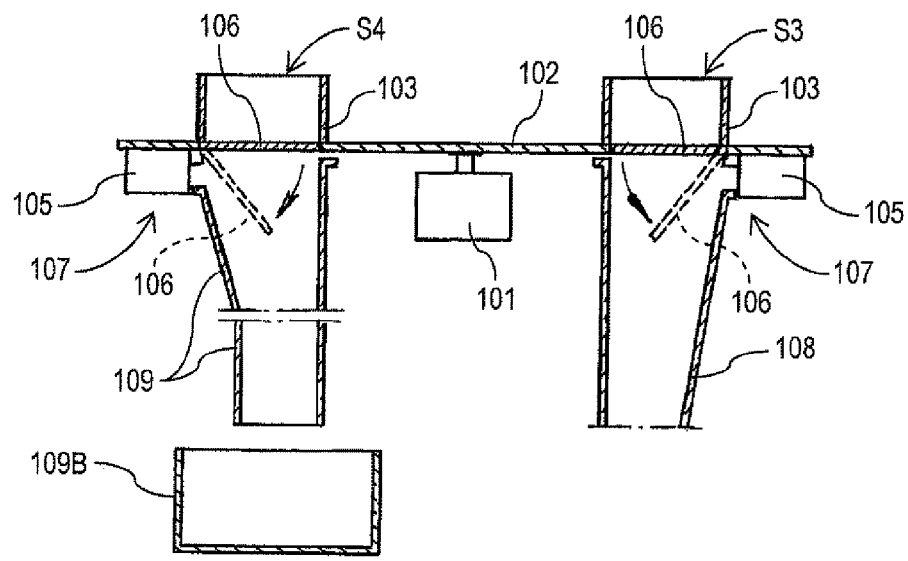
FIG. 14 is an explanatory diagram of an opening and closing device for opening and closing a bottom of the inspection container according to the present invention, the inspection container being placed on the turntable.

As part of a structure of the inspection device 100, as shown in FIG. 13, there are six units of the inspection containers 103 mounted on the turntable 102 with equal intervals therebetween, and as shown in FIG. 14, the inspection container 103 has openings formed both on upper and bottom surfaces thereof. With respect to the bottom surface opening, an opening and closing mechanism 107, which is provided with an opening and closing plate 106 that is caused to be opened and closed by a solenoid 105, is mounted on the turntable 102. When the solenoid 105 is not excited, the bottom surface opening of the inspection container 103 is closed by the opening and closing plate 106, and in this state, after the drugs TB for the single packaging portion, which are equivalent to the single administration dosage, are received from the hopper 17 into the inspection container 103 at the solid drug introduction position S1, an image of the drugs TB is captured by the imaging device 104 at the imaging position S2. The result of the imaging is compared with the prescription data, and when the result is same as the prescription data, a control is performed to fill the drugs TB into the small sachet SS section of the packaging sheet S using the packaging device 18, and when the result is different from the prescription data, a control is performed to dispose of the drugs TB.

In the control portion 120, the number of the solid drugs according to the prescription data (data regarding types of drugs and a number of solid drugs for a single packaging portion, namely, a single administration dosage, patient names, administration dates, administration periods, etc.) is stocked in one of memory portions of the storage portion 127. Further, the control portion 120 inputs a drug detection signal from the drug detection sensor 180, detects the number of the drugs TB for each type of the drugs TB using the drug detection sensor 180, the drugs TB being discharged from the tablet cases 6, counts the number, and stores the number in one of the memory portions of the storage portion 127. Meanwhile, the number of the drugs TB captured by the imaging device 104 is also stored in one of the other memory portions of the storage portion 127. When the number of the drugs TB for each type of the drugs TB discharged from the tablet cases 6 is not as specified by the prescription, numbers allocated to the tablet cases 6 concerned are displayed together with an error message.

The control portion 120 determines whether or not the number of the solid drugs according to the prescription data is same as the number of the drugs TB captured by the imaging device 104 using determination means, and when it is determined that the number of the imaged drugs TB is same as the number of the solid drugs specified by the prescription data, based on the operation of the control portion 120, the inspection container 103 is moved to the filling position S3 by rotating the turntable 102 in the normal direction using the electric operation mechanism 101 that is formed by the motor. At the filling position S3, based on the operation of the control portion 120, the solenoid 105 is energized to open the opening and closing plate 106, the drugs TB in the inspection container 103 are introduced to the nozzle 44 from a guiding chute 108 and filled into the small sachet SS section of the packaging sheet S by the packaging device 18.

On the other hand, based on the above-described determination by the control portion 120, when it is determined, on the basis of the imaging performed by the imaging device 104, that the number of the imaged drugs TB is different from the number of the solid drugs specified by the prescription data, based on the operation of the control portion 120, the inspection container 103 is moved to the disposal position S4 by rotating the turntable 102 either in the normal or reverse direction using the electric operation mechanism 101. At the disposal position S4, based on the operation of the control portion 120, the solenoid 105 is energized to open the opening and closing plate 106, so that the drugs TB in the inspection container 103 are introduced from a disposal chute 109 to a drug disposal container 109B.

FIG. 15 shows one form of printing that is performed by the printer unit 43 on the surface of the packaging sheet S. On a section of the surface corresponding to the small sachet SS (one divided package) of the packaging sheet S, a name, an administration year, month, and day, an administration time of day, etc. are printed in black, and further, the administration time of day is displayed while being color-coded by a black line L1, which is printed on a divided package SS that is administered at "Night" before sleep, a blue line L2, which is printed on the divided package SS that is administered at "Noon" after lunch, and a yellow line L3, which is printed on the divided package SS that is administered in the "Morning" after breakfast. This is provided to effectively prevent an occurrence of incorrect administration of the drugs by using the color-coding that makes the administration periods of the drugs TB easily identifiable.

Figure 16:
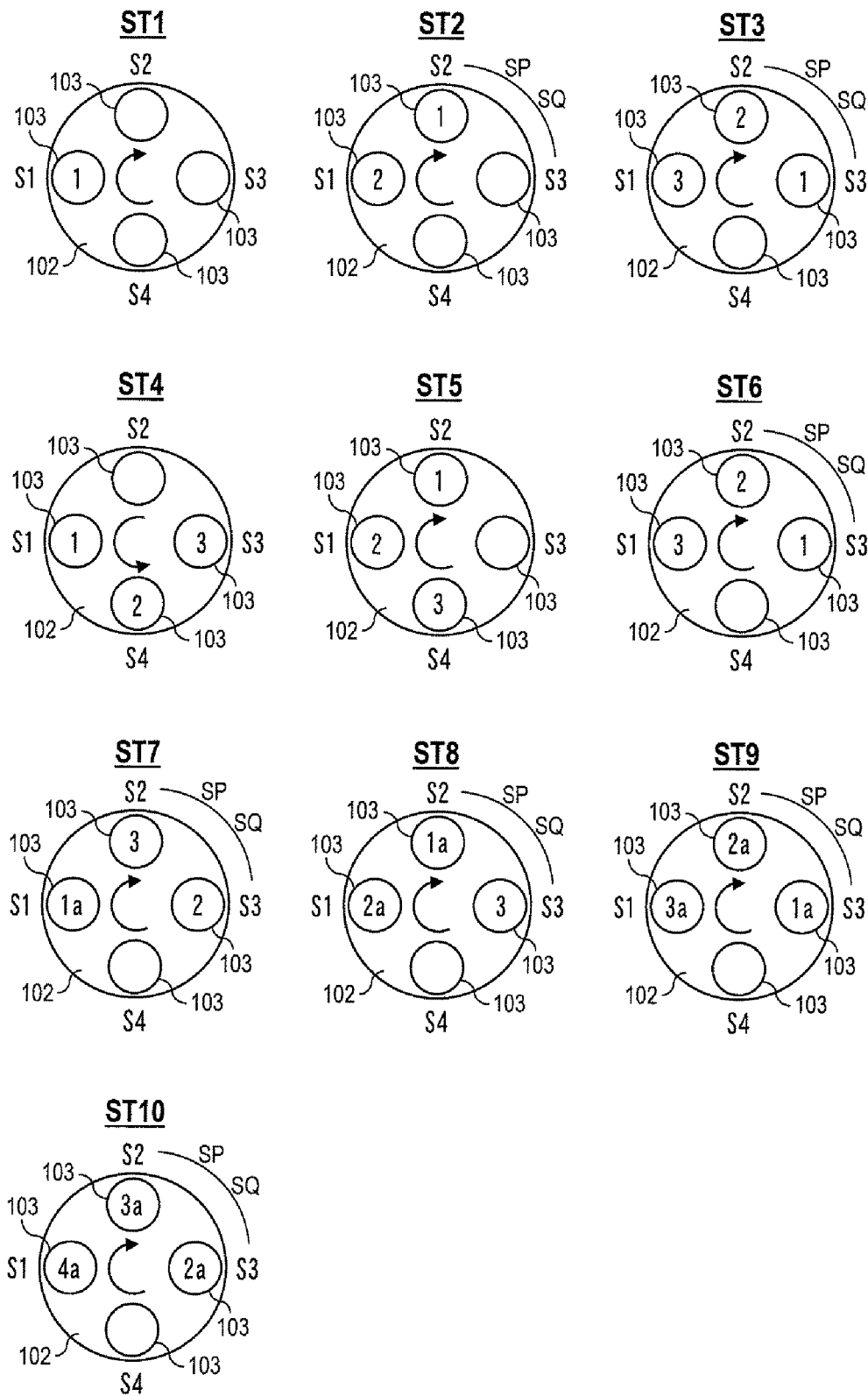
FIG. 16 is an explanatory diagram of operational steps of the inspection device according to the present invention.

FIG. 16 shows an operational step ST, which shows an operational sequence of the inspection device 100, at operational steps ST1 to ST10 according to the operational sequence. FIG. 16 shows a case in which the administration periods are set as "Morning," "Noon," and "Night," the number of the drugs TB taken at "Morning," "Noon," and "Night" is supplied to the hopper 17 by the single packaging portion (the single administration dosage) at one time, and the single packaging portion of the drugs TB is filled and packaged into each of the small sachets SS. Further, reference numerals 1 to 3 are provided in the inspection containers 103 at the positions S1, S2, S3, and S4, in which the reference numeral 1 indicates the drugs TB to be administered in the "Morning," the reference numeral 2 indicates the drugs TB to be administered at "Noon," and the reference numeral 3 indicates the drugs TB to be administered at "Night."

At the operational step ST1, the drugs TB, which are based on the prescription for the "Morning" administration, are introduced from the hopper 17 into the inspection container 103 with the reference numeral 1 positioned at the solid drug introduction position S1. At the operational step ST2, an image of the number of the drugs TB in the inspection container 103 with the reference numeral 1, which is moved to the imaging position S2 by rotating the turntable 102 in the normal direction, is captured by the imaging device 104, and also, the drugs TB, which are based on the prescription for the "Noon" administration, are introduced from the hopper 17 into the inspection container 103 with the reference numeral 2 positioned at the solid drug introduction position S1. As a result of the imaging of the drugs TB in the inspection container 103 with the reference numeral 1, when it is determined, on the basis of the determination by the control portion 120, that the number of the drugs TB in the inspection container 103 with the reference numeral 1 is same as the number of the solid drugs specified by the prescription data, based on the operation of the control portion 120, the inspection container 103 with the reference numeral 1 is caused to stay at the imaging position S2 or the inspection container 103 with the reference numeral 1 is moved to the filling position S3 by rotating the turntable 102 in the normal direction as shown at the operational step ST3 and caused to stand by in that position. In that state, the packaging sheet S is conveyed in a predetermined manner, the predetermined prescription information is printed on the surface of the section corresponding to the small sachet SS of the packaging sheet S (the section indicated as SS1 in FIG. 15) by the printer unit 43 at the printing step SP on the basis of the prescription data for the "Morning" administration, and as shown in FIG. 15, the sections S11 and S31 are sealed by heat so that the section corresponding to a small sachet SS1 of the packaging sheet S is formed by the heat sealing head 45. After the heat-sealing, the inspection container 103 with the reference numeral 1, which is caused to stay at the imaging position S2, is moved to the filling position S3 by rotating the turntable 102 in the normal direction as shown at the operational step ST3. Further, with respect to the inspection container 103 with the reference numeral 1, which has already been moved to the filling position S3 and caused to stand by in that position, at the filling position S3, as a result of the opening and closing plate 106 being opened by energizing the solenoid 105 corresponding to the inspection container 103 with the reference numeral 1, the drugs TB in the inspection container 103 with the reference numeral 1 are introduced from the guiding chute 108 to the nozzle 44 and filled into the small sachet SS section of the packaging sheet S (the section indicated as SS1 in FIG. 15) by the packaging device 18.

At the operational step ST3, as the inspection container 103 with the reference numeral 1 moves to the filling position S3, an image of the number of the drugs TB in the inspection container 103 with the reference numeral 2, which is moved to the imaging position S2, is captured, and also, the drugs TB based on the prescription for the "Night" administration are introduced from the hopper 17 to the inspection container 103 with the reference numeral 3 positioned at the solid drug introduction position S1.

After the image of the number of the drugs TB in the inspection container 103 with the reference numeral 2, which is moved to the imaging position S2, is captured, based on the operation of the control portion 120, when it is determined that the number of the drugs TB in the inspection container 103 with the reference numeral 2 is not the number of the solid drugs specified by the prescription data, the inspection container 103 with the reference numeral 2 is moved to the disposal position S4 by rotating the turntable 102 in the reverse direction. This state is the operational step ST4, and the inspection container 103 with the reference numeral 1 and the inspection container 103 with the reference numeral 3 are set in a state shown at the operational step ST4. At the disposal position S4, based on the operation of the control portion 120, as a result of the opening and closing plate 106 being opened by energizing the solenoid 105 corresponding to the inspection container 103 with the reference numeral 2 for a predetermined period of time, the drugs TB in the inspection container 103 with the reference numeral 2 are introduced from the disposal chute 109 to the drug disposal container 109B.

At the operational step ST4, since it has already been determined that the drugs TB according to the correct number of the solid drugs for the "Morning" administration have been introduced to the inspection container 103 with the reference numeral 1, which is moved to the solid drug introduction position S1, the drugs TB are not introduced thereinto at this step. Further, with respect to the inspection container 103 with the reference numeral 3, which is moved to the filling position S3, the drugs TB are already introduced thereinto, but an image of the drugs TB has not yet been captured. Therefore, the solenoid 105 is not energized at this step so that the bottom surface opening of the inspection container 103 remains closed by the opening and closing plate 106 and the drugs TB remain stored inside the inspection container 103 with the reference numeral 3.

As described above, at the operational step ST4, after the operation of disposing of the drugs TB in the inspection container 103 with the reference numeral 2 to the disposal chute 109, the turntable 102 is rotated in the normal direction, and thus, the inspection container 103 with the reference numeral 2 is positioned at the solid drug introduction position S1 indicated by the operational step ST5. In this state, based on the operation of the control portion 120, the drugs TB based on the prescription for the "Noon" administration are once more introduced from the hopper 17 into the inspection container 103 with the reference numeral 2 positioned at the solid drug introduction position S1. Along with this, although the inspection container 103 with the reference numeral 1 is moved to the imaging position S2, since an image of the inspection container 103 has already been captured, an image of the inspection container 103 is not captured once more in that position. Further, with respect to the inspection container 103 with the reference numeral 3 that is moved to the disposal position S4, since an image of the drugs TB, which are already introduced into the inspection container 103, has not yet been captured, the solenoid 105 is not energized at this step so that the bottom surface opening of the inspection container 103 remains closed by the opening and closing plate 106 and the drugs TB remain stored in the inspection container 103 with the reference numeral 3.

Then, at the operational step ST5, after once more introducing the drugs TB based on the prescription for the "Noon" administration into the inspection container 103 with the reference numeral 2, the operation advances to the operational step ST6, and an image of the drugs TB in the inspection container 103 with the reference numeral 2, which is moved to the imaging position S2, is captured. At the operational step ST6, although the inspection container 103 with the reference numeral 1 is moved to the filling position S3, since the drugs TB in the inspection container 103 are in a state of being introduced from the guiding chute 108 to the nozzle 44 as a result of the opening operation of the opening and closing plate 106, which is caused by energizing the solenoid 105, the opening operation of the opening and closing plate 106 is not performed again by energizing the solenoid 105. As a matter of course, as the printing operation by the printer unit 43 and the heat sealing operation by the heat sealing head 45 have already been performed with respect to the "Morning" administration in this state, those operations are not performed at this step. Further, since the drugs TB have already been introduced into the inspection container 103 with the reference numeral 3, which is moved to the solid drug introduction position S1, the solenoid 105 is not energized so as to maintain the state. Therefore, the bottom surface opening of the inspection container 103 remains closed by the opening and closing plate 106 and the drugs TB remain stored in the inspection container 103 with the reference numeral 3.

At the operational step ST6, based on the operation of the control portion 120, when it is determined that the number of the imaged drugs TB in the inspection container 103 with the reference numeral 2 is same as the number of the solid drugs specified by the prescription data, based on the operation of the control portion 120, the inspection container 103 with the reference numeral 2 is caused to stay at the imaging position S2 or the inspection container 103 with the reference numeral 2 is moved to the filling position S3 and caused to stand by in that position by rotating the turntable 102 in the normal direction, as shown at the operational step ST7. In that state, the packaging sheet S is conveyed in the predetermined manner, the predetermined prescription information is printed by the printer unit 43 on the surface of the section corresponding to the small sachet SS of the packaging sheet S (a section indicated as SS2 in FIG. 15) at the printing step SP on the basis of the prescription data for the "Noon" administration, and further, as shown in FIG. 15, the section S10, which is located between the small sachets SS1 and SS2, and the section S30, which closes the opening SG of the small sachet SS1, are sealed by heat by the heat sealing head 45 so that the section corresponding to the small sachet SS2 of the packaging sheet S is formed by the heat sealing head 45. After the heat-sealing, the inspection container 103 with the reference numeral 2, which is caused to stay at the imaging position S2, is moved to the filling position S3 by rotating the turntable 102 in the normal direction as shown at the operational step ST7. Further, with respect to the inspection container 103 with the reference numeral 2 that has already been moved to the filling position S3, at the filling position S3, the solenoid 105 corresponding to the inspection container 103 with the reference numeral 2 is energized so as to open the opening and closing plate 106, and the drugs TB in the inspection container 103 with the reference numeral 2 are introduced from the guiding chute 108 to the nozzle 44 and filled into the small sachet SS section of the packaging sheet S (the section indicated by SS2 in FIG. 15) by the packaging device 18.

At the operational step ST7, as the inspection container 103 with the reference numeral 2 is moved to the filling position S3, an image of the number of the drugs TB in the inspection container 103 with the reference numeral 3, which is moved to the imaging position S2, is captured, and also, the drugs TB based on a prescription for the "Morning" administration on the next day are introduced from the hopper 17 to an inspection container 103 with a reference numeral 1a positioned at the solid drug introduction position S1. Based on the operation of the control portion 120, as a result of the imaging, when it is determined that the number of the drugs TB in the inspection container 103 with the reference numeral 3 is same as the number of the solid drugs specified by the prescription data, the inspection container 103 with the reference numeral 3 is caused to stay at the imaging position S2 as shown at the operational step ST7, or the inspection container 103 with the reference numeral 3 is moved to the filling position S3 and caused to stand by in that position by rotating the turntable 102 in the normal direction, as shown at the operational step ST8. In that state, the packaging sheet S is conveyed in the predetermined manner, the predetermined prescription information is printed by the printer unit 43 on the surface of the section corresponding to the small sachet SS of the packaging sheet S (a section indicated by SS3 in FIG. 15) at the printing step SP on the basis of the prescription data for the "Night" administration, and further, as shown in FIG. 15, the section S10, which is located between the small sachets SS2 and SS3, and the section S30, which closes the opening SG of the small sachet SS2, are sealed by heat by the heat sealing head 45 so that the section corresponding to the small sachet SS3 of the packaging sheet S is formed by the heat sealing head 45. After the heat-sealing, the inspection container 103 with the reference numeral 3, which is caused to stay at the imaging position S2, is moved to the filling position S3 by rotating the turntable 102 in the normal direction as shown at the operational step ST8. Further, with respect to the inspection container 103 with the reference numeral 3 that has already been moved to the filling position S3 and caused to stand by in that position, at the filling position S3, the solenoid 105 corresponding to the inspection container 103 with the reference numeral 3 is energized to open the opening and closing plate 106, and the drugs TB in the inspection container 103 with the reference numeral 3 are introduced from the guiding chute 108 to the nozzle 44 and filled into the small sachet SS section of the packaging sheet S (the section indicated as SS3 in FIG. 15) by the packaging device 18.

At the operational step ST8, with respect to the inspection container 103 with the reference numeral 1a that is newly moved to the imaging position S2, an image of the number of the drugs TB stored therein is captured. Further, the drugs TB based on a prescription for the "Noon" administration on the next day are introduced from the hopper 17 into the inspection container 103 with a reference numeral 2a, which is newly positioned at the solid drug introduction position S1.

Next, at the operational step ST8, as a result of the imaging, when it is determined that the number of the drugs TB in the inspection container 103 with the reference numeral 1a is same as the number of the solid drugs specified by the prescription data, based on the operation of the control portion 120, the inspection container 103 with the reference numeral 1a is caused to stay at the imaging position S2 or the inspection container 103 with the reference numeral 1a is moved to the filling position S3 and caused to stand by in that position by rotating the turntable 102 in the normal direction, as shown at the operational step ST9. In that state, the packaging sheet S is conveyed in the predetermined manner, the predetermined prescription information is printed by the printer unit 43 on the surface of the section corresponding to the small sachet SS of the packaging sheet S (a section indicated by SS1 at the left end of FIG. 15) at the printing step SP on the basis of the prescription data for the "Morning" administration on the next day, and further the section S10, which is located between the small sachets SS1 and SS3, and the section S30, which closes the opening SG of the small sachet SS3, are sealed by heat by the heat sealing head 45 so that the section (the section indicated as SS1 at the left end of FIG. 15) corresponding to the small sachet SS1 of the packaging sheet S is formed by the heat sealing head 45 in the same manner as described above. The required position of the packaging sheet S is sealed by heat. After the heat-sealing, the inspection container 103 with the reference numeral 1a, which is caused to stay at the imaging position S2, is moved to the filling position S3 by rotating the turntable 102 in the normal direction, as shown at the operational step ST9. Further, with respect to the inspection container 103 with the reference numeral 1a that has already been moved to the filling position S3 and caused to stand by in that position, at the filling position S3, the solenoid 105 corresponding to the inspection container 103 with the reference numeral 1a is energized to open the opening and closing plate 106, and the drugs TB in the inspection container 103 with the reference numeral 1a are introduced from the guiding chute 108 to the nozzle 44 and filled into the small sachet SS section of the packaging sheet S (the section indicated as SS1 at the left end of FIG. 15) by the packaging device 18 in the same manner as described above.

At the operational step ST9, as the inspection container 103 with the reference numeral 1a is moved to the filling position S3, an image of the number of the drugs TB in the inspection container 103 with the reference numeral 2a, which is moved to the imaging position S2, is captured, and also, the drugs TB based on a prescription for the "Night" administration on the next day are introduced from the hopper 17 to the inspection container 103 with a reference numeral 3a positioned at the solid drug introduction position S1. Based on the operation of the control portion 120, as a result of the imaging, when it is determined that the number of the drugs TB in the inspection container 103 with the reference numeral 2a is same as the number of the solid drugs specified by the prescription data, the inspection container 103 with the reference numeral 2a is caused to stay at the imaging position S2 as shown at the operational step ST9 or the inspection container 103 with the reference numeral 2a is moved to the filling position S3 and caused to stand by in that position by rotating the turntable 102 in the normal direction, as shown at the operational step ST10. In that state, the packaging sheet S is conveyed in the predetermined manner, the predetermined prescription information is printed by the printer unit 43 on the surface of the section corresponding to the small sachet SS of the packaging sheet S at the printing step SP on the basis of the prescription data for the "Noon" administration on the next day, and further, in the same manner as described above, the required position of the packaging sheet S is sealed by heat using the heat sealing head 45. After the heat-sealing, the inspection container 103 with the reference numeral 2a, which is caused to stay at the imaging position S2, is moved to the filling position S3 by rotating the turntable 102 in the normal direction, as shown at the operational step ST10. Further, with respect to the inspection container 103 with the reference numeral 2a that is already moved to the filling position S3 and caused to stand by in that position, at the filling position S3, the solenoid 105 corresponding to the inspection container 103 with the reference numeral 2a is energized to open the opening and closing plate 106, and the drugs TB in the inspection container 103 with the reference numeral 2a are introduced from the guiding chute 108 to the nozzle 44 and filled into the small sachet SS section of the packaging sheet S by the packaging device 18.

At the operational step ST10, with respect to the inspection container 103 with the reference numeral 3a that is newly moved to the imaging position S2, an image of the number of the drugs TB stored therein is captured. Further, the drugs TB based on a prescription for the "Morning" administration on the day after next are introduced from the hopper 17 to the inspection container 103 with a reference numeral 4a, which is newly positioned at the solid drug introduction position S1. The above-described operations are repeated after this, and as a result of the imaging, when it is determined that the number of the drugs TB in the inspection container 103 with the reference numeral 3a is same as the number of the solid drugs specified by the prescription data, in accordance with the same operations as described above, based on the operation of the control portion 120, the drugs TB in the inspection container 103 are filled into the small sachet SS of the packaging sheet S by the packaging device 18. Further, when_it is determined that the number of the drugs TB is not as specified by the prescription data, the drugs TB are disposed of at the disposal position S4, then, the correct number of the drugs TB for the single packaging portion is once more discharged from the tablet cases 6, and the same determination as described above is performed by performing the imaging process at the imaging position S2 again in which an image of the drugs TB discharged from the tablet cases 6 is once more captured.

With the above-described structure, operations of the drug supply device 1 of the present invention will be described. Note that the shutters 16 are closed in a power-on state. Further, inside an upper structural body 3, the shelves 5, on which the tablet cases 6 are mounted, are mounted in the above-described manner, the tablet cases 6 respectively storing predetermined drugs.

When the power of the drug supply device 1 is turned on, the control portion 120 reads the identification codes of the respective tablet cases 6 in the shelves 5, which are located at left and right ends of the upper structural body 3, using the identification sensors 33. By this, the control portion 120 stores data regarding the types of the drugs TB stored in the respective tablet cases 6 along with positional information of the respective tablet cases 6, and those data are also transmitted to the PC.

Note that the control portion 120 has a database regarding the types of the drugs TB in the respective tablet cases 6 and the positional information of the respective tablet cases 6, and the database is also transmitted to the PC. Then, the identification codes read by the identification sensors 33 are also added to the database.

Next, a drug preparation operation will be described. When an operator inputs prescription data (data for a single administration dosage, namely, data regarding types and quantities of drugs for a single packaging portion, administration dates, administration periods, patient names, etc.) on the basis of a prescription from a doctor using the above-described PC, the PC for the drug supply device 1 identifies tablet cases 6, in which the drugs TB specified by the prescription data are stored, from the above-described database. Further, the drug supply device 1 discharges the drugs inside the vertical grooves 24 into a discharge port 210 one by one by rotating the drive motor 14 in the normal direction using the motor driver 124 and then by rotating (normal rotation) the discharge drum 23.

At that time, the control portion 120 inputs the drug detection signal from the drug detection sensor 180 and counts the number of the discharged drugs TB. Then, at a stage at which a predetermined amount of the drugs TB is discharged, the control portion 120 stops the drive motor 14. The discharged drugs TB enter into the drop chute 15, which is formed by the pathway 13, from the discharge chute 19, and the drugs TB for the single administration dosage (the single packaging portion) are temporarily received by the left and right shutters 16.

Then, the control portion 120 opens the opening and closing plates 63A and 63B by energizing the shutter solenoid 123 in the above-described manner (FIG. 9) and causes the drugs TB to drop into the hopper 17, so that the drugs TB are introduced into the inspection container 103 of the inspection device 100 as described above. In a state in which the drugs TB for the single administration dosage (the single packaging portion) are introduced from the hopper 17 into the corresponding inspection container 103 in the above-described manner, when the operation of the inspection device 100 determines that the number of the drugs TB is same as the number of the solid drugs specified by the prescription data, the drugs TB in the inspection container 103, which is moved to the filling position S3, are introduced from the guiding chute 108 to the nozzle 44 and then filled into the packaging sheet S by the packaging device 18. Further, after being separately packaged into the packaging sheet S for each of the administration periods of Morning, Noon, and Night, the drugs TB are delivered to the removal opening 21. In addition, as described above, the printing of the prescription information regarding the drugs TB to be packaged is performed by the printer unit 43 before introducing the drugs TB into the small sachet of the packaging sheet S.

In the present invention, as described above, the inspection container 103 receives the drugs TB from the hopper 17 at the solid drug introduction position S1, is moved to the imaging position S2, and then, when it is determined that the number of the solid drugs is as specified by the prescription data on the basis of the imaging performed by the imaging device 104, the inspection container 103 is moved to the filling position S3. On the other hand, when it is determined that the number of the solid drugs is not as specified by the prescription data on the basis of the imaging performed by the imaging device 104, the inspection container 103 is moved to the disposal position S4, and after the drugs TB are disposed of thereat, is moved to the solid drug introduction position S1, and newly receives the drugs TB from the hopper 17 into the inspection container 103 at the solid drug introduction position S1. Further, the inspection container 103 is moved to the imaging position S2, and based on another determination on whether the number of the solid drugs is as specified by the prescription data or not, the determination being performed on the basis of the imaging performed by the imaging device 104, the inspection container 103 is moved to either the filling position S3 or the disposal position S4 in the same manner as described above.

Therefore, as a result of respectively arranging the solid drug introduction position S1, the imaging position S2, the filling position S3, and the disposal position S4 in the normal and reverse directions of the turntable 102, for example, when the drugs are filled into the packaging sheet S or a bottle for each of the administration periods of Morning, Noon, and Night, both an inspection on the drugs for the "Morning" administration and an inspection on the drugs for the "Noon" administration can be performed simultaneously. Consequently, the inspection time is shortened and a preferable effect is expected in terms of shortening a time required for a series of the drug filling processes.

Although the above-described embodiment has a structure in which the inspection container 103 receives the drugs TB from the hopper 17 at the solid drug introduction position S1, since the object of the present invention is to include the inspection device 100 provided with the control portion 120 that determines whether the number of the drugs TB discharged from the tablet cases 6 matches the number of the solid drugs specified by the prescription data before separately packaging the drugs TB into the divided packaging sheet S, the drugs TB being discharged from the tablet cases 6 on the basis of the desired prescription data, the inspection device 100 having the above-described structure is not limited to the arrangement described in the above-described embodiment. For example, the inspection device 100 may be provided below each of the shutters 16, then, the drugs, which are received by the shutters 16 as a result of the turntable 102 being rotated, may be introduced into the inspection container 103 from the shutters 16 at the solid drug introduction position S1, and subsequent inspection operations may be performed in the same manner as described above.

In the above-described embodiment, if the determination result, which determines that the number of the solid drugs is as specified by the prescription data, is obtained after imaging the number of the solid drugs in the inspection container 103 a plurality of times and when all the plurality of the image data match the prescription data, accuracy of the determination can be improved. Further, when the number of the drugs in the inspection container 103 is determined, if colors or shapes of the drugs are added as determination criteria, the accuracy of the determination can be further improved.

Although the above-described embodiment has a mechanism in which, when it is determined that the number of the drugs in the inspection container 103 is as specified by the prescription data on the basis of the inspection result of the inspection device 100, the inspection container 103 is moved to the filling position S3 and then the drugs TB in the inspection container 103 are packaged by being introduced into the small sachet of the packaging sheet S, instead of using the packaging sheet S, it is possible to fill the drugs TB for a plurality of administration dosages into a drug container such as a bottle. More specifically, as the drugs TB for the single administration dosage are stored in each of the inspection containers 103, even if the drugs TB in the inspection containers 103 are filled into a single unit of the above-described drug container being arranged at a position corresponding to the nozzle 44, every time that the inspection container 103 is moved to the filling position S3, the gist of the present invention does not change. Therefore, the above-described packaging device 18 has a mechanism in which the drugs TB for a predetermined number of administration dosages (for example, administration dosages for three days with three administration periods of Morning, Noon, and Night per one day) are filled into the above-described drug container, and the drug container is conveyed to the removal opening 21. In this manner, since the packaging device 18 according to the present invention can be applied either to a case in which the drugs TB are packaged by being introduced into the small sachet of the packaging sheet S or to a case in which the drugs TB are filled into the drug container as described above, when the present invention includes both of the applications in which the drugs TB may be filled into the packaging sheet S or the drug container, the packaging device can be called as the filling device.

REFERENCE SIGNS LIST 1 drug supply device
2 main body (case)
8 front door
16 shutter
17 hopper
18 packaging device (filling device)
42 sheet feeding board
43 printer unit (printing portion)
44 nozzle (drug filling portion)
45 heat sealing head (packaging portion)
46 feed roller (conveyance mechanism)
47 cutter
48 conveyor unit
53 first conveyance roller
54 movable roller
55 second conveyance roller
100 inspection device
101 electric operation mechanism
102 turntable
103 inspection container
120 control portion
180 drug detection sensor
S packaging sheet (sheet)
S1 solid drug introduction position
S2 imaging position
S3 filling position
S4 disposal position

The invention claimed is:

1. A drug supply device comprising:
a plurality of tablet cases in which solid drugs are stored while being categorized by type;
a hopper that collects single administration solid drugs, which are solid drugs for a single administration dosage, discharged from the tablet cases on the basis of predetermined prescription data;
an inspection device that inspects the single administration solid drugs discharged by the hopper; and
a packaging device that fills and packages the single administration solid drugs inspected by the inspection device into a packaging sheet, wherein:
the inspection device includes:
an inspection container that holds the single administration solid drugs discharged from the hopper;
a movement mechanism that moves the inspection container; and
an imaging device that captures an image of the single administration solid drugs in the inspection container,
based on a result that the inspection device inspects the single administration solid drugs by which the imaging device captures the image of the single administration solid drugs in the inspection container, the single administration solid drugs are disposed of toward a disposal container, when a number of the single administration solid drugs is different from the prescription data, and the single administration solid drugs are packaged by the packing device, when the number of the single administration solid drugs is same as the prescription data, and
the movement mechanism includes an introduction position at which the single administration solid drugs are discharged from the hopper into the inspection container, an imaging position at which an image of the single administration solid drugs in the inspection container is captured by the imaging device, a disposal position at which the single administration solid drugs are disposed of, and a filling position at which the single administration solid drugs are discharged into the packaging device.

2. The drug supply device according to claim 1, wherein:
the movement mechanism is formed by a turntable and an electric operation mechanism that rotatably supports the turntable, and
the turntable includes a plurality of inspection containers on an upper surface of the turntable.

3. The drug supply device according to claim 2, wherein the disposal position is arranged at a position that is opposite to the imaging position with respect to the introduction position.

4. The drug supply device according to claim 3, wherein, when the number of the single administration solid drugs is different from the prescription data, the drug supply device moves the inspection container to the disposal position and disposes of the single administration solid drugs at the disposal position, and after that, the drug supply device moves the inspection container to the introduction position, discharges a new set of solid drugs for the single administration dosage based on the prescription data from the tablet cases, and discharges the new set of solid drugs for the single administration dosage from the hopper into the inspection container.

5. The drug supply device according to claim 2, wherein, when the number of the single administration solid drugs is different from the prescription data, the drug supply device moves the inspection container to the disposal position and disposes of the single administration solid drugs at the disposal position, and after that, the drug supply device moves the inspection container to the introduction position, discharges a new set of solid drugs for the single administration dosage based on the prescription data from the tablet cases, and discharges the new set of solid drugs for the single administration dosage from the hopper into the inspection container.

6. The drug supply device according to claim 1, wherein the disposal position is arranged at a position that is opposite to the imaging position with respect to the introduction position.

7. The drug supply device according to claim 6, wherein, when the number of the single administration solid drugs is different from the prescription data, the drug supply device moves the inspection container to the disposal position and disposes of the single administration solid drugs at the disposal position, and after that, the drug supply device moves the inspection container to the introduction position, discharges a new set of solid drugs for the single administration dosage based on the prescription data from the tablet cases, and discharges the new set of solid drugs for the single administration dosage from the hopper into the inspection container.

8. The drug supply device according to claim 1, wherein, when the number of the single administration solid drugs is different from the prescription data, the drug supply device moves the inspection container to the disposal position and disposes of the single administration solid drugs at the disposal position, and after that, the drug supply device moves the inspection container to the introduction position, discharges a new set of solid drugs for the single administration dosage based on the prescription data from the tablet cases, and discharges the new set of solid drugs for the single administration dosage from the hopper into the inspection container.

9. A drug supply device comprising:
 a plurality of tablet cases in which solid drugs are stored while being categorized by type;
 a hopper that collects solid drugs discharged from the tablet cases on the basis of predetermined prescription data;
 an inspection device that inspects the solid drugs discharged by the hopper; and
 a packaging device that fills and packages the solid drugs inspected by the inspection device into a packaging sheet, wherein:
 an inspection device is arranged in a pathway through which the solid drugs are conveyed from the tablet cases to the packaging device, the inspection device includes a turntable, and the turntable includes an inspection container into which the solid drugs discharged from the tablet cases are introduced;
 the turntable is configured to be rotated by an electric operation mechanism to a solid drug introduction position at which the solid drugs are introduced from the hopper into the inspection container, an imaging position at which an image of the solid drugs in the inspection container is captured by an imaging device, a filling position at which the solid drugs in the inspection container can move toward the packaging device, and a disposal position at which the solid drugs are disposed of from inside the inspection container;
 the inspection container receives the solid drugs from the hopper at the solid drug introduction position and moves to the imaging position;
 when it is determined that the number of the solid drugs is as specified by the prescription data on the basis of the imaging performed by the imaging device, the inspection container is moved to the filling position; and
 when it is determined that the number of the solid drugs is not as specified by the prescription data on the basis of the imaging, the inspection container is moved to the disposal position, and after the solid drugs are disposed of toward a disposal container at the disposal position, the inspection container is moved to the solid drug introduction position, the inspection container newly receives the solid drugs from the hopper at the solid drug introduction position and moves to the imaging position, and based on another determination as to whether or not the number of the solid drugs is as specified by the prescription data made on the basis of the imaging performed by the imaging device, the inspection container is moved to either the filling position or the disposal position in the same manner as described above.

10. A drug inspection method performing a process in a solid drug supply device that includes a plurality of tablet cases in which solid drugs are stored while being categorized by type, an inspection device including an inspection container and a movement mechanism that moves the inspection container and a packaging device that fills and packages single administration solid drugs, which are solid drugs for a single administration dosage, discharged from the tablet cases on the basis of desired prescription data into a packaging sheet, the drug inspection method comprising:
 a collecting step of collecting, at an introduction position of the movement mechanism, the single administration solid drugs discharged from a hopper into the inspection container;
 an imaging step of capturing, at an imaging position of the movement mechanism, an image of the single administration solid drugs in a state in which the single administration solid drugs discharged from the tablet cases are received is included at a stage before the single administration solid drugs discharged from the tablet cases on the basis of the desired prescription data are delivered to the packaging device;
 based on the imaging, when it is determined that a number of the single administration solid drugs is as specified by the prescription data, the single administration solid drugs are moved to a filling step at which the single administration solid drugs can be delivered to the packaging device at a filling position of the movement mechanism; and
 based on the imaging, when it is determined that the number of the single administration solid drugs is not as specified by the prescription data, the single administration solid drugs are moved to a disposal step at which the single administration solid drugs are disposed of, at a disposal position of the movement mechanism, toward a disposal container, and after the single administration solid drugs are disposed of, a new set of solid drugs for the single administration dosage is caused to be discharged from the tablet cases according to specified by the prescription data, and capturing an image of the new set of solid drugs for the single administration dosage discharged from the tablet cases is conducted at the imaging step again.

* * * * *